United States Patent
Astarita

(10) Patent No.: US 11,237,154 B2
(45) Date of Patent: Feb. 1, 2022

(54) METABOLIC PATHWAY AND METABOLITE IDENTIFICATION

(71) Applicant: Waters Technologies Corporation, Milford, MA (US)

(72) Inventor: Giuseppe Astarita, Hopkinton, MA (US)

(73) Assignee: Waters Technologies Corporation, Milford, MA (US)

( * ) Notice: Subject to any disclaimer, the term of this patent is extended or adjusted under 35 U.S.C. 154(b) by 297 days.

(21) Appl. No.: 15/577,695

(22) PCT Filed: May 26, 2016

(86) PCT No.: PCT/US2016/034298
§ 371 (c)(1),
(2) Date: Nov. 28, 2017

(87) PCT Pub. No.: WO2016/196183
PCT Pub. Date: Dec. 8, 2016

(65) Prior Publication Data
US 2018/0164292 A1    Jun. 14, 2018

Related U.S. Application Data

(60) Provisional application No. 62/167,991, filed on May 29, 2015.

(51) Int. Cl.
*G01N 33/50* (2006.01)
*B01D 15/08* (2006.01)
(Continued)

(52) U.S. Cl.
CPC ......... *G01N 33/5038* (2013.01); *B01D 15/08* (2013.01); *G01N 24/14* (2013.01);
(Continued)

(58) Field of Classification Search
CPC ...... G01N 33/5038; G01N 30/72; G16B 5/00; G16B 20/00; G16B 40/00; G16C 20/20
See application file for complete search history.

(56) References Cited

U.S. PATENT DOCUMENTS

2003/0229451 A1* 12/2003 Hamilton ........... G01N 30/8655
702/19
2010/0312487 A1* 12/2010 Yamaguchi ............ G01N 27/62
702/23
(Continued)

OTHER PUBLICATIONS

Shuzhao et al; "Predicting Network Activity from High Throughput Metabolomics", PLOS Computational Biology, 2013. (Year: 2013).*
(Continued)

*Primary Examiner* — Regis J Betsch
*Assistant Examiner* — Jeremy A Delozier
(74) *Attorney, Agent, or Firm* — Womble Bond Dickinson (US) LLP; Deborah M. Vernon

(57) ABSTRACT

The present disclosure relates to methods and apparatus for identifying metabolic pathways and metabolites in complex biological samples. In particular, the present disclosure relates to a method and apparatus to increase the confidence of metabolite identification in metabolomics, such as in untargeted metabolomics data, using various statistical tools, such as over representation and enrichment analysis.

11 Claims, 15 Drawing Sheets

(51) Int. Cl.
G16B 5/00 (2019.01)
G16B 20/00 (2019.01)
G16B 40/00 (2019.01)
G16C 20/20 (2019.01)
G16B 40/10 (2019.01)
G16B 20/20 (2019.01)
G01N 24/14 (2006.01)
G01N 30/72 (2006.01)
G01N 30/86 (2006.01)

(52) U.S. Cl.
CPC ......... *G01N 30/72* (2013.01); *G01N 30/8617* (2013.01); *G01N 30/8675* (2013.01); *G16B 5/00* (2019.02); *G16B 20/00* (2019.02); *G16B 20/20* (2019.02); *G16B 40/00* (2019.02); *G16B 40/10* (2019.02); *G16C 20/20* (2019.02); *G01N 2570/00* (2013.01)

(56) References Cited

U.S. PATENT DOCUMENTS

2014/0273069 A1    9/2014  West et al.
2015/0160231 A1*   6/2015  Meitei ............... G01N 33/6851
                                                            702/22
2017/0082578 A1*   3/2017  Kobold .............. H01J 49/0031

OTHER PUBLICATIONS

Xia et al; "MetPA_Web-based Metabolomics Tool for Pathway Analysis and Visualization", Bioinformatics Applications Note, 2010. (Year: 2010).*
Giuseppe et al; "Monitoring metabolites consumption and secretion in cultured cells using ultra-performance liquid chromatography quadrupole-time of flight mass spectrometry", Anal Bioanal Chem, 2011. (Year: 2011).*
Dettmer et al, "Mass Spectrometry-based Metabolomics", 2007. (Year: 2007).*
Ahmadiani et al. "Anthocyanins Contents, Profiles, and Color Characteristics of Red Cabbage Extracts from Different Cultivars and Maturity Stages." J. Agricultural Food Chem. 62.30(2014): 7524-7531.
Aires, A., et al., Effect of nitrogen and sulfur fertilization on glucosinolates in the leaves and roots of broccoli sprouts (*Brassica oleracea* var. italica). Journal of the Science of Food and Agriculture 2006, 86, (10), 1512-1516.
Armah, C. N., et al. A diet rich in high-glucoraphanin broccoli interacts with genotype to reduce discordance in plasma metabolite profiles by modulating mitochondria' function. The American journal of clinical nutrition 2013, 98, (3), 712-722.
Astarita, G., et al., An emerging role for metabolomics in nutrition science. J Nutrigenet Nutrigenomics 2013, 6, (4-5), 181-200.
Awad, A. B., et al., Phytosterols as anticancer dietary components: evidence and mechanism of action. The Journal of nutrition 2000, 130, (9), 2127-2130.
Berdyshev, E. V., Mass spectrometry of fatty aldehydes. Biochimica et Biophysica Acta (BBA)—Molecular and Cell Biology of Lipids 2011, 1811, (11), 680-693.
Calder, P. C., et al., Understanding omega-3 polyunsaturated fatty acids. Postgraduate medicine 2009, 121, (6), 148-157.
Cartea, M. E., et al., Glucosinolates in *Brassica* foods: bioavailability in food and significance for human health. Phytochemistry reviews 2008, 7, (2), 213-229.
Cartea, M. E., et al., Phenolic compounds in *Brassica* vegetables. Molecules 2011, 16, (1), 251-80.
Cavill, R., et al., Consensus-phenotype integration of transcriptomic and metabolomic data implies a role for metabolism in the chemosensitivity of tumour cells. PLoS Comput Biol 2011, 7, (3), e1001113.

Chory, J., et al., From seed germination to flowering, light controls plant development via the pigment phytochrome. Proceedings of the National Academy of Sciences 1996, 93, (22), 12066-12071.
Ciska, E., et al., Content of glucosinolates in cruciferous vegetables grown at the same site for two years under different climatic conditions. Journal of Agricultural and Food Chemistry 2000, 48, (7), 2862-2867.
Clouse, S. D., et al., Brassinosteroids: essential regulators of plant growth and development. Annual review of plant biology 1998, 49, (1), 427-451.
Dong, W., et al., Ultra-performance Liquid Chromatography-High-definition Mass Spectrometry Analysis of Constituents in the Root of Radix Stemonae and those Absorbed in Blood after Oral Administration of the Extract of the Crude Drug. Phytochemical Analysis 2012, 23, (6), 657-667.
Eugeni Pillar et al., Chloroplast lipid droplet type II NAD(P)H quinone oxidoreductase is essential for prenylquinone metabolism and vitamin K1 accumulation. Proc Natl Acad Sci U S A 2011, 108, (34), 14354-9.
Fahey, J. W., et al., Broccoli sprouts: an exceptionally rich source of inducers of enzymes that protect against chemical carcinogens. Proceedings of the National Academy of Sciences 1997, 94, (19), 10367-10372.
Fahy, E., et al., Update of the LIPID MAPS comprehensive classification system for lipids. Journal of lipid research 2009, 50, (Supplement), S9-S14.
Fiehn, 0., Metabolomics—the link between genotypes and phenotypes. Plant molecular biology 2002, 48, (1-2), 155-171.
Fu et al. "UPLC-UV-MSE analysis for quantification and identification of major carotenoid and chlorophyll species in algae." Analytical and bioanalytical chemistry 2012, 404, (10), 3145-3154.
Glueck, C. J., et al., Relationships of serum plant sterols (phytosterols) and cholesterol in 595 hypercholesterolemic subjects, and familial aggregation of phytosterols, cholesterol, and premature coronary heart disease in hyperphytosterolemic probands and their first-degree relatives. Metabolism 1991, 40, (8), 842-848.
Gombos, Z. et al., The unsaturation of membrane lipids stabilizes photosynthesis against heat stress. Plant Physiology 1994, 104, (2), 563-567.
Gonzales, G. B., et al., Ultra (high)-pressure liquid chromatography-electrospray ionization-time-of-flight-ion mobility-high definition mass spectrometry for the rapid identification and structural characterization of flavonoid glycosides from cauliflower waste. Journal of Chromatography A 2014, 1323, 39-48.
Goodspeed et al. "Postharvest Circadian Entrainment Enhances Crop Pest Resistance and Phytochemical Cycling." Curr. Biol. 23(2013): 1235-1241.
Gorelik, S., et al., Lipid peroxidation and coupled vitamin oxidation in simulated and human gastric fluid inhibited by dietary polyphenols: health implications. Journal of agricultural and food chemistry 2005, 53, (9), 3397-3402.
Guo, R., et al., Effect of sucrose and mannitol on the accumulation of health-promoting compounds and the activity of metabolic enzymes in broccoli sprouts. Scientia Horticulturae 2011, 128, (3), 159-165.
Guzman, I., et al., Simultaneous extraction and quantitation of carotenoids, chlorophylls, and tocopherols in *Brassica* vegetables. Journal of agricultural and food chemistry 2012, 60, (29), 7238-7244.
Hollman, P. C. et al., Dietary flavonoids: intake, health effects and bioavailability. Food and Chemical Toxicology 1999, 37, (9), 937-942.
Jahangir et al. "Health-Affecting Compounds in Brassicaceae." Comprehensive reviews in food science and food safety. 8.2(2009): 31-43.
Jahangir, M., et al., Metal ion-inducing metabolite accumulation in *Brassica rapa*. J Plant Physiol 2008, 165, (14), 1429-37.
Jones et al. "Dietary phytosterols as cholesterol-lowering agents in humans." Can. J. Physiol. Pharma. 75.3(1997): 217-227.
Klyachko-Gurvich, G. L., et al., Desaturation of fatty acids as an adaptive response to shifts in light intensity 1. Physiologia Plantarum 1999, 107, (2), 240-249.

(56) References Cited

OTHER PUBLICATIONS

Li, F., et al. MPINet: metabolite pathway identification via coupling of global metabolite network structure and metabolomic profile. Biomed Res Int 2014, 2014, 325697.
Maldini, M. et al., A liquid chromatography-mass spectrometry approach to study "glucosinoloma" in broccoli sprouts. Journal of Mass Spectrometry 2012, 47, (9), 1198-1206.
Martinis, J., et al., A novel method for prenylquinone profiling in plant tissues by ultra-high pressure liquid chromatography-mass spectrometry. Plant Methods 2011, 7, (1), 23.
McConn et al. "The Critical Requirement for Linolenic Acid is Pollen Development, Not Photosynthesis, in an *Arabidopsis* Mutant." Plant Cell. 8(1996): 403-416.
Moreno, D. A., et al.,Chemical and biological characterisation of nutraceutical compounds of broccoli. Journal of pharmaceutical and biomedical analysis 2006, 41, (5), 1508-1522.
Pacini, T., et al., Multidimensional Analytical Approach Based on UHPLC-UV-Ion Mobility-MS for the Screening of Natural Pigments. Anal Chem 2015.
Paglia, G., et al., Ion mobility derived collision cross sections to support metabolomics applications. Anal Chem 2014, 86, (8), 3985-93.
Paglia, G., et al., Ion mobility-derived collision cross section as an additional measure for lipid fingerprinting and identification. Anal Chem 2015, 87, (2), 1137-44.
Park, W. T., et al. Metabolic profiling of glucosinolates, anthocyanins, carotenoids, and other secondary metabolites in kohlrabi (*Brassica oleracca* var. gongylodes). Journal of agricultural and food chemistry 2012, 60, (33), 8111-8116.
Perez-Balibrea, S., et al., Genotypic effects on the phytochemical quality of seeds and sprouts from commercial broccoli cultivars. Food chemistry 2011, 125, (2), 348-354.
Perez-Balibrea, S., et al., Glucosinolates in broccoli sprouts (*Brassica oleracea* var. italica) as conditioned by sulphate supply during germination. Journal of food science 2010, 75, (8), C673-C677.
Perez-Balibrea, S., et al., Influence of light on health-promoting phytochemicals of broccoli sprouts. Journal of the Science of Food and Agriculture 2008, 88, (5), 904-910.
Phillip, D., et al., Quenching of chlorophyll fluorescence in the major light-harvesting complex of photosystem II: a systematic study of the effect of carotenoid structure. Proceedings of the National Academy of Sciences 1996, 93, (4), 1492-1497.
Plumb, G. W. et al., Antioxidant properties of the major polyphenolic compounds in broccoli. Free Radical Research 1997, 27, (4), 429-435.
Podsedek, A., Natural antioxidants and antioxidant capacity of *Brassica* vegetables: A review. LWT—Food Science and Technology 2007, 40, (1), 1-11.
Quanbeck, S. M., et al. Metabolomics as a hypothesis-generating functional genomics tool for the annotation of *Arabidopsis thaliana* genes of "unknown function". Frontiers in plant science 2012, 3.
Sies, H.; et al., Non-Nutritive Bioactive Food Constituents of Plants: Lycopene, Lutein and Zeaxanthin. International journal for vitamin and nutrition research 2003, 73, (2), 95-100.
Simopoulos, A. P., Essential fatty acids in health and chronic disease. The American Journal of Clinical Nutrition 1999, 70, (3), 560s-569s.
Smith et al. "A metabolite mass spectral database." Ther Drug Monit 2005, 27, (6), 747-51.
Extended European Search Report relating to corresponding application: PCT/US2016034298 completed on Nov. 8, 2018 and dated Nov. 22, 2018.
Li, S., et al., "Predicting Network Activity from High Throughput Metabolomics," PLOS Computational Biology, 9:7, 1-11 (2013).
Stahl et al. "Bioactivity and protective effects of natural carotenoids." Biochim. Biophys Acta (BBA)—Molecular Basis of Disease. 1740. 2(2005): 101-107.

Stopka, S. A., et al., Metabolic transformation of microalgae due to light acclimation and genetic modifications followed by laser ablation electrospray ionization mass spectrometry with ion mobility separation. Analyst 2014, 139, (22), 5946-5954.
Sun et al. "Profiling the indole alkaloids in yohimbe bark with ultra-performance liquid chromatography coupled with ion mobility quadrupole time-of-flight mass spectrometry." Rapid Commun. Mass Spectrom. 25.18(2011): 2591-2602.
Sun, H., et al., Metabolomics study on Fuzi and its processed products using ultra-performance liquid-chromatography/electrospray-ionization synapt high-definition mass spectrometry coupled with pattern recognition analysis. Analyst 2012, 137, (1), 170-185.
Sun, J., Profiling Polyphenols in Five *Brassica* Species Microgreens by UHPLC-PDA-ESI/HRMS n. Journal of agricultural and food chemistry 2013, 61, (46), 10960-10970.
Talalay, P., et al., Phytochemicals from cruciferous plants protect against cancer by modulating carcinogen metabolism. J Nutr 2001, 131, (11 Suppl), 3027S-33S.
Traka et al. "Glucosinolates, isothiocyanates and human health." Phytochem. Rev. 8.1(2009): 269-282.
Vallejo et al. "Glucosinolates and vitamin C content in edible parts of broccoli florets after domestic cooking." Eur. Food Res. Technol. 215.4(2002): 310-316.
Velasco et al. "Phytochemical fingerprinting of vegetable *Brassica oleracea* and *Brassica napus* by simultaneous identification of glucosinolates and phenolics." Phytochem. Anal. 22.2(2011): 144-152.
Verkerk, R., et al., Glucosinolates in *Brassica* vegetables: the influence of the food supply chain on intake, bioavailability and human health. Molecular nutrition & food research 2009, 53, (S2), S219-S219.
Vershinin, A., Biological functions of carotenoids—diversity and evolution. Biofactors 1999, 10, (2), 99-104.
Wishart, D. S., et al., HMDB 3.0—The Human Metabolome Database in 2013. Nucleic Acids Res 2013, 41, (Database issue), D801-7.
Xia, J., MetaboAnalyst2.0 a comprehensive server for metabolomic data analysis. Nucleic acids research 2012, 40, (W1), W127-W133.
Zhang, Y., The molecular basis that unifies the metabolism, cellular uptake and chemopreventive activities of dietary isothiocyanates. Carcinogenesis 2012, 33, (1), 2-9.
Xia et al. 'MetPA: a web-based metabolomics tool for pathway analysis and visulization', Bioinformatics Applications Note, 2010, vol. 26, pp. 2342-2342, col. 2 para 1-4; p. 2343. col. 2, para 1, Figure 1; Abstract.
Paglia et al. 'Monitoring metabolites consumption and secretion in cultured cells using ultra-performace liquid chromatography quadrupole time of flight mass spectrometry (UPLC-Q-ToF-MS)', Analytical Bioanalytical Chemistry, 2012, Vo. 402, pp. 1183-1198. abstract; p. 1183, col. 2, para 3; p. 1184, col. 1, para 3 to col. 2, para 2; p. 1185, Table 1; p. 1187, col. 1, para 3-5, col. 2, para 3; p. 1196, col. 1, para 1; p. 1197. col. 1, para 2-3.
Xia et al. 'Web-based inference of biological patterns, functions and pathways from metabolomic data using MetaboAnalyst', Nature Protocols, 2011, vol. 6, pp. 743-760. Entire Document.
Astarita et al. Targeted lipidomics strategies for oxygenated metabolites of polyunsaturated fatty acids, Biochim Biophys Acta. Apr. 2015, vol. 1851(4), pp. 456-468. Entire Document.
International Search Report and Written Opinion for International Application No. PCT/US2016/034298, dated Jul. 24, 2016 and dated Sep. 7, 2016.
Search Report issued in European Application No. 16804058.2 dated Jan. 23, 2020.
Maldini et al. "Metabolomics of Broccoli Sprouts Using UPLC with Ion Mobility Enabled LC/MSe and TransOmics Informatics." Application Notes, Waters Technologies Corporation. (2013): 64-71.

\* cited by examiner

FIG. 3 Multiple identifications for each altered feature are found searching databases by accurate mass

| Compound | Neutral mass | m/z | z | Retention time | Peak Width | Accepted ID | Identifications | Anova (p) | Max fold change | Highest mean | Lowest mean | Tag | Isotope distribution | Max Abundance | N |
|---|---|---|---|---|---|---|---|---|---|---|---|---|---|---|---|
| •4.29_719.5655m/z | <unknown> | 719.5655 | 1 | 4.29 | 0.12 | | 25 | 2.11E-15 | Infinity | pcDNAFlag T6h | hGadd45bFlag T20min | | | 106.5530 | 1 |
| ○3.63_690.5060m/z | <unknown> | 690.5060 | 1 | 3.63 | 0.08 | | 40 | 2.92E-14 | Infinity | hGadd45bFlag T0 | hGadd45bFlag T20min | | | 55.7674 | 3 |
| ○4.08_798.5595m/z | <unknown> | 798.5595 | 1 | 4.08 | 0.08 | | 29 | 1.7E-13 | Infinity | hGadd45bFlag T6h | hGadd45bFlag T20min | | | 64.7943 | 1 |
| ○6.77_549.4873m/z | <unknown> | 549.4873 | 1 | 6.77 | 0.14 | | 6 | 1.9E-13 | Infinity | hGadd45bFlag T6h | pcDNAFlag T20min | | | 175.2781 | 4 |
| ○4.12_736.5678m/z | <unknown> | 736.5678 | 1 | 4.12 | 0.11 | | 7 | 3.39E-13 | 160 | hGadd45bFlag T0 | pcDNAFlag T20min | | | 95.1967 | 1 |
| ○3.76_708.5518m/z | <unknown> | 708.5518 | 1 | 3.76 | 0.09 | | 13 | 4.29E-13 | Infinity | hGadd45bFlag T6h | hGadd45bFlag T20min | | | 84.0708 | 1 |
| ○7.85_509.4926m/z | <unknown> | 509.4926 | 1 | 7.85 | 0.10 | | 0 | 1.05E-12 | Infinity | hGadd45bFlag T0 | hGadd45bFlag T20min | | | 84.9099 | 4 |
| ○0.96_672.3419m/z | <unknown> | 672.3419 | 1 | 0.96 | 0.05 | | 0 | 1.44E-12 | Infinity | hGadd45bFlag T0 | hGadd45bFlag T20min | | | 48.9193 | 5 |
| ○10.76_942.6480m/z | <unknown> | 942.6480 | 1 | 10.76 | 0.29 | | 1 | 4.73E-12 | Infinity | hGadd45bFlag T6h | hGadd45bFlag T20min | | | 946.3134 | 5 |
| ○1.20_990.6630m/z | 990.6630 | 991.6709 | 1 | 1.20 | 0.08 | | 1 | 4.77E-12 | Infinity | hGadd45bFlag T6h | pcDNAFlag T20min | | | 899.3436 | 4 |
| ○4.05_769.5413m/z | <unknown> | 769.5413 | 1 | 4.05 | 0.09 | | 18 | 1.06E-11 | Infinity | hGadd45bFlag T6h | pcDNAFlag T20min | | | 84.8750 | 2 |
| ○13.04_340.2969n | 340.2969 | 341.3047 | 1 | 13.04 | 0.08 | | 4 | 1.36E-11 | 218 | hGadd45bFlag T0 | pcDNAFlag T20min | | | 112.5733 | 4 |
| ○9.44_789.0028m/z | <unknown> | 789.0028 | 1 | 9.44 | 0.17 | | 0 | 1.38E-11 | Infinity | hGadd45bFlag T6h | hGadd45bFlag T20min | | | 426.8183 | 4 |
| ○13.70_339.2899n | <unknown> | 339.2899 | 1 | 13.70 | 0.24 | | 4 | 1.61E-11 | 1.42E+03 | hGadd45bFlag T6h | pcDNAFlag T20min | | | 321.8786 | 3 |
| ○1.21_496.5154m/z | <unknown> | 496.5154 | 1 | 1.21 | 0.08 | | 0 | 2E-11 | Infinity | pcDNAFlag T6h | hGadd45bFlag T20min | | | 474.2949 | 3 |
| ○13.46_1009.7268m/z | <unknown> | 1009.7268 | 1 | 13.46 | 0.16 | | 0 | 2.36E-11 | Infinity | pcDNAFlag T6h | hGadd45bFlag T20min | | | 391.9472 | 2 |
| ○13.05_970.6806m/z | <unknown> | 970.6806 | 1 | 13.05 | 0.11 | | 0 | 4.09E-11 | Infinity | hGadd45bFlag T0 | hGadd45bFlag T20min | | | 187.3482 | 6 |
| ○5.38_862.4998m/z | <unknown> | 862.4998 | 1 | 5.38 | 0.10 | | 1 | 4.17E-11 | Infinity | pcDNAFlag T20min | hGadd45bFlag T0 | | | 587.5029 | 1 |

FIG. 3 continued

Compound 4.29_719.5655m/z

| Compound ID | Description | Adducts | Formula | Retention time | Score | Mass error (ppm) | Isotope similarity | Link |
|---|---|---|---|---|---|---|---|---|
| LMGP04020073 | PG(O-18:0/16:0) | M+H-$H_2O$ | $C_{40}H_{81}O_9P$ | | 57.5 | 8.69 | 82.25 | www.lipi... |
| LMGP04020080 | PG(O-16:0/18:0) | M+H-$H_2O$ | $C_{40}H_{81}O_9P$ | | 57.5 | 8.69 | 82.25 | www.lipi... |
| LMGP04020043 | PG(O-20:0/14:0) | M+H-$H_2O$ | $C_{40}H_{81}O_9P$ | | 57.5 | 8.69 | 82.25 | www.lipi... |
| LMGP10010196 | PA(16:0/21:0) | M+H | $C_{40}H_{79}O_8P$ | | 57.5 | 8.96 | 82.47 | www.lipi... |
| LMGP10010154 | PA(15:0/22:0) | M+H | $C_{40}H_{79}O_8P$ | | 57.5 | 8.96 | 82.47 | www.lipi... |
| LMGP10010315 | PA(18:0/19:0) | M+H | $C_{40}H_{79}O_8P$ | | 57.5 | 8.96 | 82.47 | www.lipi... |
| LMGP10010702 | PA(22:0/15:0) | M+H | $C_{40}H_{79}O_8P$ | | 57.5 | 8.96 | 82.47 | www.lipi... |
| LMGP10010679 | PA(21:0/16:0) | M+H | $C_{40}H_{79}O_8P$ | | 57.5 | 8.96 | 82.47 | www.lipi... |
| LMGP10010968 | PA(17:0/20:0) | M+H | $C_{40}H_{79}O_8P$ | | 57.5 | 8.96 | 82.47 | www.lipi... |
| LMGP10010513 | PA(20:0/17:0) | M+H | $C_{40}H_{79}O_8P$ | | 57.5 | 8.96 | 82.47 | www.lipi... |
| LMGP10010868 | PA(19:0/18:0) | M+H | $C_{40}H_{79}O_8P$ | | 57.5 | 8.96 | 82.47 | www.lipi... |
| LMGL02010300 | DG(22:3(10Z,13Z,16Z)/22 | M+H | $C_{47}H_{74}O_5$ | | 56.9 | 5.66 | 77.10 | www.lipi... |
| LMGL02010301 | DG(22:4(7Z,10Z,13Z,16Z) | M+H | $C_{47}H_{74}O_5$ | | 56.9 | 5.66 | 77.10 | www.lipi... |

Isobaric & near-isobaric species
Database search at <10ppm
Some exogenous, chemicals, etc Current protocols require that we assign an absolute identification before we can proceed, missing the opportunity to use pathways information to determine covariance within same pathways.

FIG. 5A
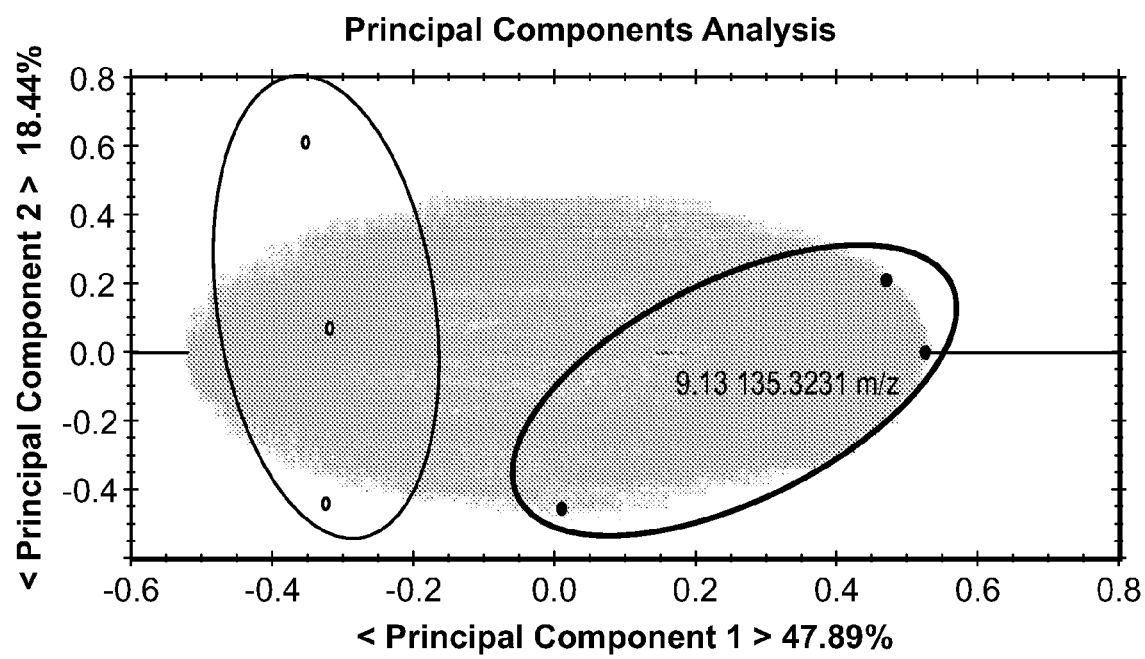
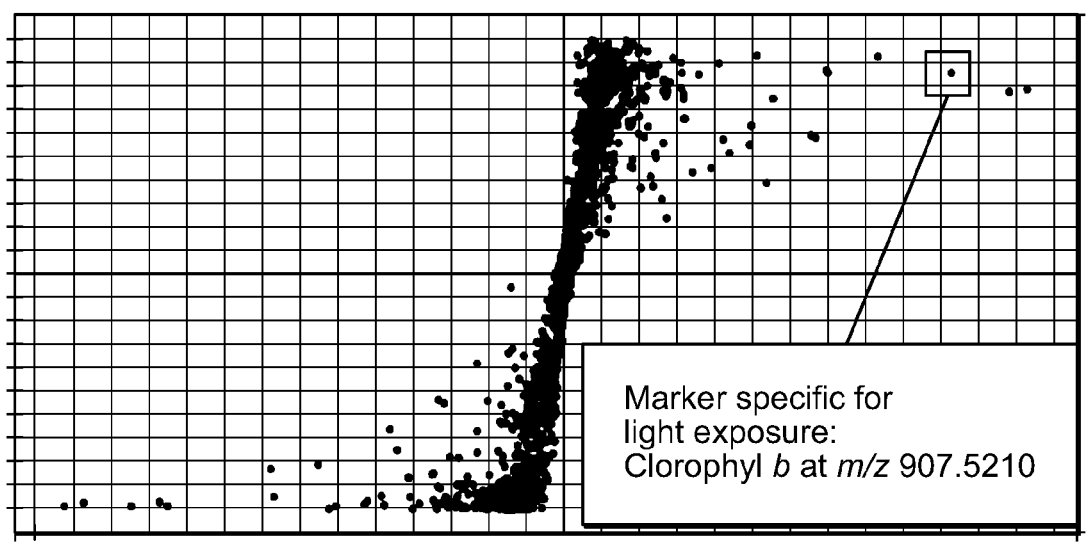

FIG. 6B
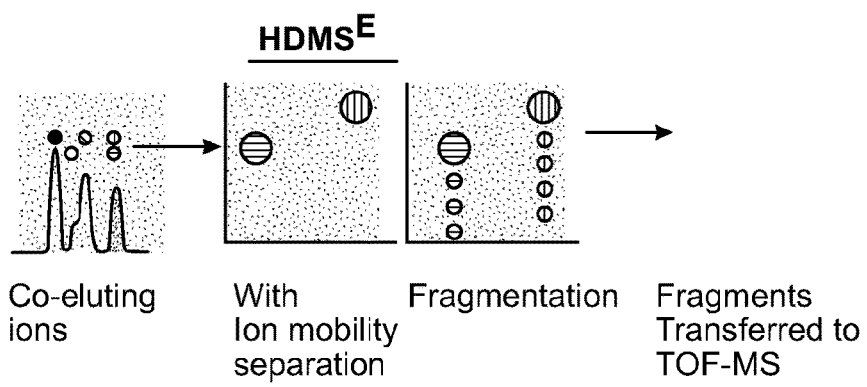
Co-eluting ions → With Ion mobility separation → Fragmentation → Fragments Transferred to TOF-MS
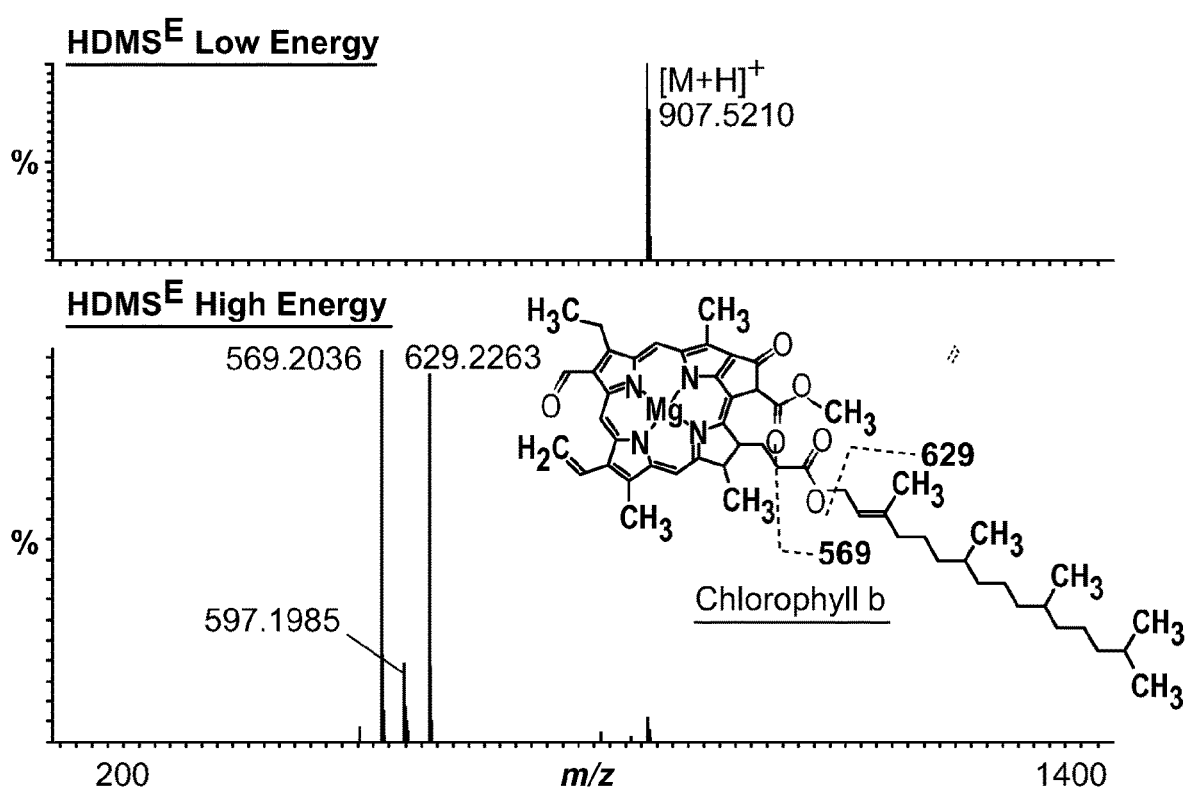

FIG. 7C

| # | Pathway name | p-value* | FDR* | p-value# | Q-value# | Impact Score |
|---|---|---|---|---|---|---|
| 1 | Steroid biosynthesis | 1.11E-16 | 2.85E-15 | 8.14E-16 | 1.45E-12 | 0.5926 |
| 2 | Diterpenoid biosynthesis | 1.16E-06 | 1.67E-05 | 0.152 | 1 | 0.47745 |
| 3 | Indole alkaloid biosynthesis/Tryptophan metabolism | 1.53E-01 | 2.33E-06 | 4.76E-09 | 3.61E-07 | 0.2 |
| 4 | Porphyrin and chlorophyll metabolism | 7.25E-17 | 2.85E-15 | 0.000952 | 0.0305 | 0.13305 |
| 5 | Carotenoid biosynthesis/Retinol metabolism | 4.11E-07 | 7.06E-06 | 0.000834 | 0.0277 | 0.07913 |
| 6 | Arachidonic acid metabolism | 2.00E-39 | 1.72E-37 | 1.09E-19 | 3.89E-16 | 0 |
| 7 | Biosynthesis of unsaturated fatty acids | 1.70E-06 | 2.04E-05 | 0.0106 | 0.248 | 0 |

FIG. 8A
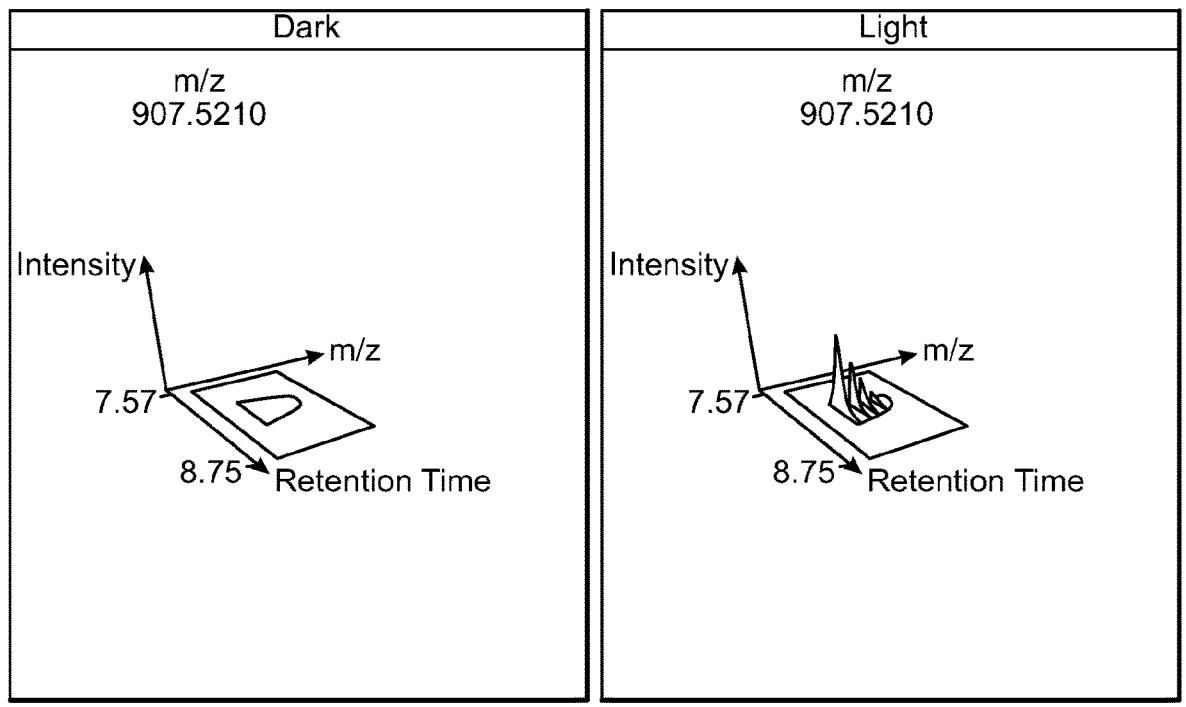
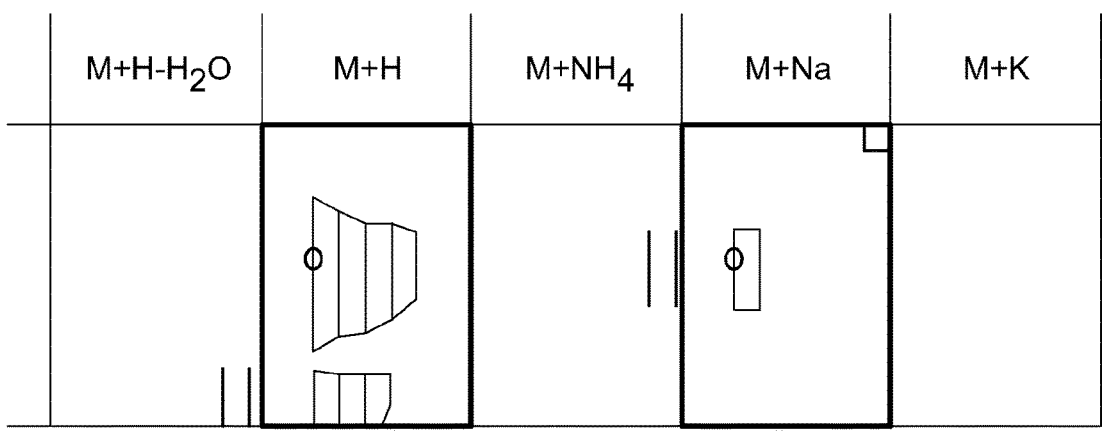

METABOLIC PATHWAY AND METABOLITE IDENTIFICATION

CROSS-REFERENCE TO RELATED APPLICATIONS

This application is a National Stage Application of International Application No. PCT/US2016/034298 filed May 26, 2016, which claims the benefit of and priority to U.S. Provisional Patent Application No. 62/167,991, filed on May 29, 2015, the entire contents of each of which are incorporated herein by reference.

TECHNICAL FIELD

The present disclosure relates to methods and apparatus for identifying metabolic pathways and metabolites in complex biological samples. In particular, the present disclosure relates to a method and apparatus to increase the confidence of metabolic pathway and metabolite identification in metabolomics, such as in untargeted metabolomics data using various statistical tools.

BACKGROUND OF THE INVENTION

Metabolite identification is a major bottleneck for metabolomics analysis. Despite the use of modern analytical tools, such as chromatography coupled with high-resolution mass spectrometry, the identification of the vast majority of the observed peaks in any one sample remains unknown. For example, for the same retention time, exact mass and molecular formula there can be multiple, sometimes hundreds, of potential chemical structures. These potential structures can be provided as only a tentative list(s) of metabolite identifications.

It is known that metabolite changes within a sample are interconnected. The interconnection of these changes can correspond to one or more particular metabolic pathways. A sample having been exposed to a stimulus, treatment, condition, etc. can exhibit metabolite changes. The recognition of changed, or altered, metabolites can be used to identify the effects of the stimulus on the sample. The recognition of altered metabolites in a complex sample, as well as, the identification of the metabolic pathway(s) and ultimately the altered metabolites using modern analytical tools instrumentation and methodology is time consuming and resource intensive.

The present disclosure relates to methods and apparatus for identifying metabolic pathways and metabolites in complex biological samples which are less time consuming and resource intensive.

SUMMARY OF THE INVENTION

The present disclosure relates to methods and apparatus for identifying metabolic pathways and metabolites in complex biological samples. In general, the methods disclosed herein are less time consuming and resource intensive than conventional methods (e.g., on the order of minutes rather than hours or days).

In one embodiment, the present disclosure relates to a method of identifying a metabolic pathway containing two or more metabolites including (i) receiving two or more tentative metabolite identification lists, wherein each list includes potential metabolites having at least substantially the same mass measurement, (ii) comparing the two or more tentative metabolite identification lists with two or more known metabolic pathways, and (iii) identifying at least one metabolic pathway that is statistically more likely to include the two or more metabolites. The method can also be used for identifying at least one of the metabolites wherein each list corresponds to a metabolite peak, and the method can further include analyzing at least one of the metabolic peaks to identify at least one of the metabolites.

In another embodiment, the present disclosure relates to a method of identifying a metabolic pathway containing two or more metabolites, including (i) receiving a sample containing metabolites, (ii) receiving a standard containing metabolites, (iii) analyzing the sample with a mass spectrometer system to generate sample metabolite peaks, wherein each sample metabolite peak has a signal intensity, and at least a mass measurement, (iv) analyzing the standard with a mass spectrometer system to generate standard metabolite peaks, wherein each standard metabolite peak has a signal intensity and at least a mass measurement, (v) comparing the sample metabolite peaks and the standard metabolite peaks to identify one or more altered metabolite peaks having an intensity difference of greater than about 10%, (vi) generating a tentative metabolite identification list for at least two or more of the altered metabolite peaks, wherein each list includes potential metabolites having at least substantially the same mass measurement, (vii) comparing the two or more tentative metabolite identification lists with two or more known metabolic pathways, and (viii) identifying at least one metabolic pathway that is statistically more likely to include the two or more metabolites. The method can also be used for identifying at least one of the metabolites wherein each list corresponds to a metabolite peak, and the method further includes analyzing at least one of the metabolic peaks to identify at least one of the metabolite.

The above embodiments can include various features. For example the above embodiments can feature a separation component coupled to mass spectrometer of the mass spectrometry system. The separation component can comprise a quadrupole time-of-flight mass spectrometer. For example, the mass spectrometry system can include a chromatographic separation, an ion mobility separation, or both, coupled to mass spectrometer, e.g., a quadrupole time-of-flight mass spectrometer.

The step of comparing the sample metabolite peaks and the standard metabolite peaks can include analyzing the sets of peaks using multivariate statistical analyses, such as principle component analysis, correlation analysis, partial least squares discriminant analysis (PLA-DA), ANOVA analysis or combinations thereof.

The methods of the present disclosure can also feature identifying one or more potential metabolites by comparing at least the mass measurement with metabolite databases. The methods can also include the step of identifying at least one metabolic pathway comprises the use of an over-representation analysis tool.

The methods and apparatus of the present invention provide several advantages over the prior art. By testing whether sets of metabolites are enriched in particular pathways as opposed to individual metabolites, the confidence and efficiently of identifying potential pathways and metabolites is increased. For example, the present disclosure can be used with enrichment analysis on the tentative identifications lists of significantly altered peaks to determine whether related metabolites are found statistically enriched in specific metabolic pathways. Because metabolite changes are interconnected and can occur in a coordinated fashion in biology, finding multiple metabolite hits within a particular biochemical pathway can increase the probability that the identification is correct.

The identification of one or more metabolites within a particular biochemical pathway can also support the identification of one or more other metabolites within the same, or similar pathways, that may only have subtle, but significant, changes. These related metabolites can go otherwise unnoticed with conventional approaches. Likewise, the number of false positive identifications can be decreased, and the methodology can help to generate more specific hypotheses on which metabolic pathway(s) to focus for further (targeted) investigation. For example, the methodology can be applied on the entire dataset instead of exclusively on the significantly altered peaks. The use of over representation and enrichment analysis tools, including network analysis, can be used to facilitate metabolite identification in a discovery process and to reduce the false positive identification.

Finally, some embodiments of the present disclosure can utilize enrichment analysis as a tool to support and facilitate initial metabolite pathway and metabolite identification without the requirement for at least one structural elucidation beforehand the application of enrichment analysis.

BRIEF DESCRIPTION OF THE DRAWINGS

The foregoing and other features and advantages provided by the present disclosure will be more fully understood from the following description of exemplary embodiments when read together with the accompanying drawings, in which:

FIG. 3 shows the exemplary list of FIG. 2. The list shows that there are many potential metabolites having the same mass measurement for each metabolite peak based on the mass measurement, or by retention time and mass measurement. The prior art requires that an absolute identification is assigned to each metabolite peak before metabolic pathway investigation occurs. The tentative identification and the potential pathway information is not used to determine covariance within same pathways, as is used by the present disclosure.

FIG. 5 shows an exemplary statistical analysis of metabolite peaks. FIG. 5A shows a multivariate statistical analysis of UHPLC/HDMS$^E$ test data. The separated samples can be segregated into clusters using principle component analysis (PCA). (5A, top). The metabolites that contribute most to the variance among groups can be isolated using partial, least-squares discriminant analysis (PLS-DA) (5A, bottom).

FIG. 6 shows an exemplary analysis using a chromatographic separation and mass spectrometry with and without an ion mobility separation. FIG. 6B shows the system with ion mobility separation (e.g., HDMS$^E$). Both systems allow for the acquisition of both precursors and fragment spectra information with one single chromatographic run. The application of high collision energy in the transfer collision cell can allow the precursor molecules to be broken down into their constituent parts (product ions), and can allow determination of the original structure. The identification of metabolites in complex mixtures, such as the identification of the chlorophyll b structure, can be aided by the observation of characteristic fragments generated with high energy after ion-mobility separation. The addition of an ion-mobility separation of co-eluting precursor metabolites can produce a cleaner and less complex product ion spectra. As described in Example 1, the identification of chlorophyll b by searching against databases was simplified using a chromatographic separation and mass spectrometry with an ion mobility separation.

FIG. 7 shows an exemplary method of using statistical tools to select the metabolic pathways. FIG. 7C shows a summary of the major metabolic pathways altered in broccoli sprouts grown under conditions of continuous light as compared with the metabolites in sprouts grown under conditions of continuous dark. FDR refers to False Discovery Rate; p-value* refers to p-values from MPINet; p-value$^\#$ and Q-value$^\#$ refer to values from IMPaLA. The impact scores are from the topological analysis using Relative-betweeness Centrality from MetPA. The scores indicated which metabolic pathway or pathways are statistically more likely to include the metabolites.

DETAILED DESCRIPTION

Figure 1:
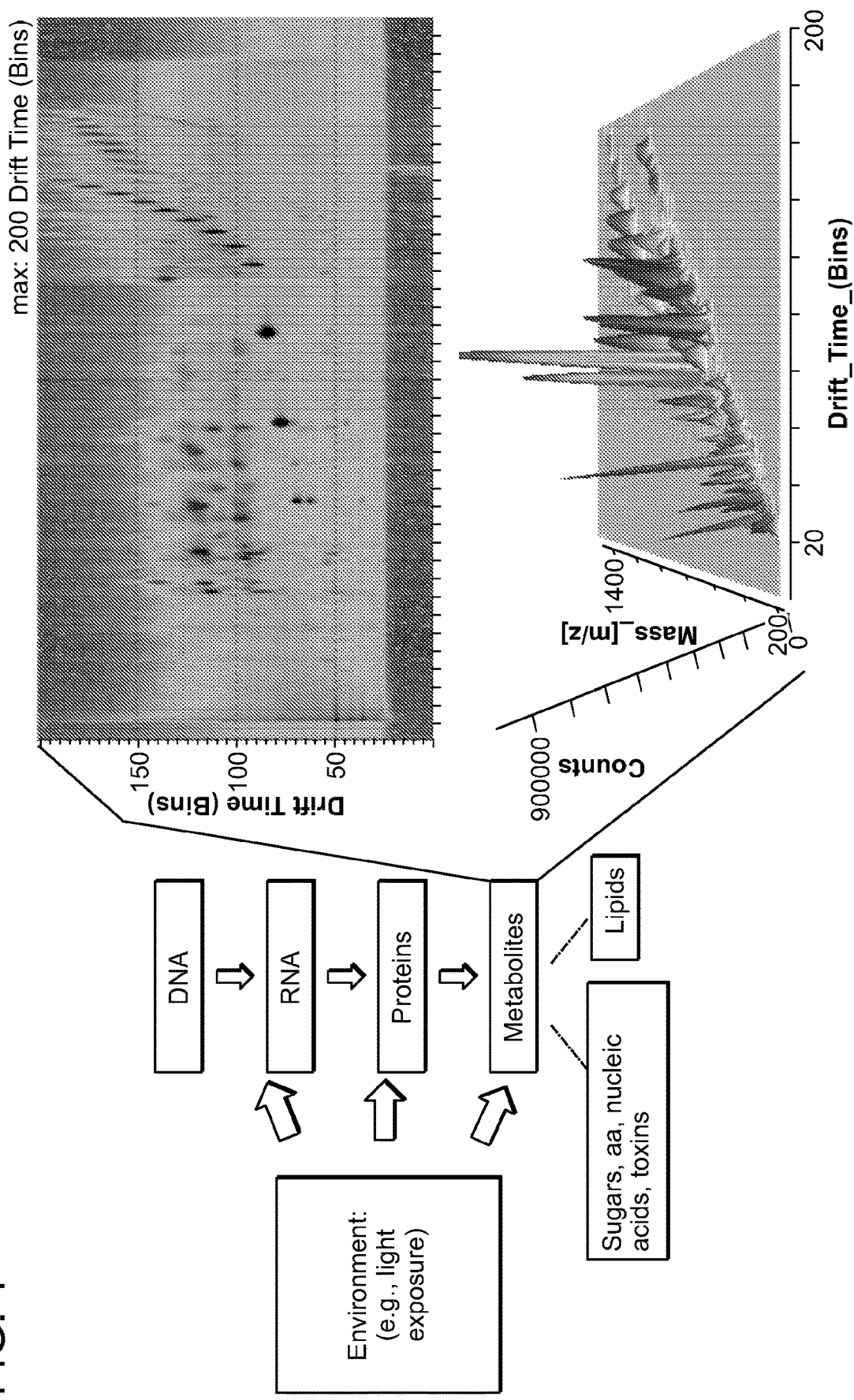
FIG. 1 shows an overview of screening a biological network. The different classes of compounds can be screened in a biological sample are shown including all of the metabolites. Metabolites can derive from both the generic imprint and from the environment (e.g., light exposure). Complex samples can contain thousands of metabolites and have a wide range of chemical complexity and concentration. The profiling of the entire set of metabolites (i.e., the metabolome) can help define the molecular phenotype of the biological system. The analysis of the untargeted metabolomics with a UHPLC system coupled with an ion mobility-enabled QTof MS is shown. After UHPLC separation, the metabolites can be further separated in another dimension using ion-mobility before MS detection. This combination of UHPLC and ion mobility can provide increased peak capacity and specificity in the quantification and identification process.
Figure 2:
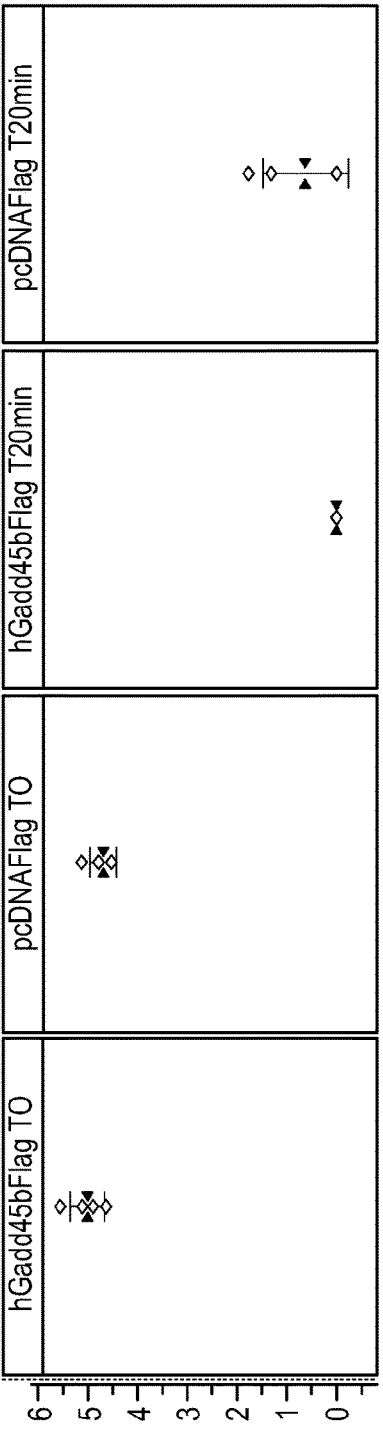
FIG. 2 shows an exemplary list of altered metabolites that can be determined from a complex sample tested against a control sample using statistical analysis.

The present disclosure relates to methods and apparatus for identifying metabolic pathways and metabolites in complex biological samples.

As used herein the term "metabolomics" refer to the study of cellular metabolites, such as the complete set of metabolites (the metabolome) in a biological sample under a given set of conditions. The metabolome is highly responsive to pathophysiological conditions and can be used to determine the effects of stimulus, etc. or changes to an organism, such as to distinguish disease phenotypes.

As used herein the term "metabolite" refers to an intermediate or product resulting from metabolism or other chemical/biological changes that occur within an organism.

As used herein the term "metabolic pathway" refers to biochemical reactions for converting (transmuting) one chemical species into another, such as anabolic or catabolic pathways. Anabolic pathways involve constructing a larger molecule from smaller molecules, a process requiring energy. Catabolic pathways involve breaking down of larger molecules, often releasing energy.

In one embodiment, the present disclosure relates to a method of identifying a metabolic pathway containing two or more metabolites, including (i) receiving two or more tentative metabolite identification lists, wherein each list includes potential metabolites having at least substantially the same mass measurement, (ii) comparing the two or more tentative metabolite identification lists with two or more known metabolic pathways, and (iii) identifying at least one metabolic pathway that is statistically more likely to include the two or more metabolites.

Each tentative identification list can include two or more potential metabolites having substantially the same mass measurement. The mass measurements of the potential metabolites on the list can be within 10 ppm of the theoretical mass value. The mass measurements of the potential metabolites can be within 20, 19, 18, 17, 16, 15, 14, 13, 12, 11, 10, 9, 8, 7, 6, 5, 4, 3, 2, 1, 0.9, 0.8, 0.7, 0.6, 0.5, 0.4, 0.3, 0.2 or about 0.1 ppm. These values can be used to define a range, such as about 15 to about 5 ppm.

Each tentative identification list having a mass measurement, or having an exact mass measurement, can be generated by any mass spectrometry instrument or apparatus capable of generated mass measurements, or exact mass measurements. For example, the mass spectrometry instrument or apparatus can be a quadrupole, time-of-flight, orbitrap, ion trap, Fourier transform ion cyclotron resonance, etc. In particular, the mass spectrometry instrument or apparatus can be a time-of-flight mass spectrometer (e.g., Xevo® G2-S Tot) or a quadrupole time-of-flight mass spectrometer.

In some embodiments, the mass spectrometry system can include a chromatographic separation, an ion mobility separation, or both, coupled to mass spectrometer, e.g., a quadrupole time-of-flight mass spectrometer.

Each tentative identification list can include two or more potential metabolites having substantially the same mass measurement and substantially the same retention time. The retention time of the potential metabolites on the list can be within (i.e., have a maximum difference between them) of about 1 second, 0.9, 0.8, 0.7, 0.6, 0.5, 0.4, 0.3, 0.2 or about 0.1 seconds. These values can be used to define a range, such as about 0.5 to about 0.1 seconds.

Each tentative identification list having a mass measurement, or having an exact mass measurement, and a retention time can be generated by any chromatography-mass spectrometry system capable of generated a separation of components having retention times and mass measurements, or exact mass measurements. For example, the chromatography-mass spectrometry system can be a quadrupole, time-of-flight, orbitrap, ion trap, Fourier transform ion cyclotron resonance, etc. In particular, the system can be a LC system, such as a UHPLC system (ACQUITY® UPLC, Waters Corporation, Milford, Mass., USA) coupled to a hybrid Q-Tof mass spectrometer (Synapt® HDMS, Waters Corporation, Milford, Mass., USA).

Each tentative identification list can include two or more potential metabolites having substantially the same mass measurement, substantially the same retention time, substantially the same drift time, or combinations thereof. The drift time of the potential metabolites on the list can be within (i.e., have a maximum difference between them) of about 2, 1, 0.8, 0.6, 0.4, 0.2 or about 0.1 milliseconds. These values can be used to define a range, such as about 1 to about 0.1 milliseconds.

Each tentative identification list having a mass measurement, or having an exact mass measurement, a retention time, and a drift time can be generated by any chromatography-separation-mass spectrometry system capable of generated a separation of components having drift times, retention times and mass measurements, or exact mass measurements. For example, the chromatography-separation-mass spectrometry system can be a quadrupole, time-of-flight, orbitrap, ion trap, Fourier transform ion cyclotron resonance, etc. In particular, the system can a LC system, such as a UHPLC system (ACQUITY® UPLC, Waters Corporation, Milford, Mass., USA) coupled with an ion-mobility-enabled quadrupole, time-of-flight (QTOF) mass spectrometer (Synapt® G2-S, Waters Corporation, Milford, Mass., USA).

The two or more lists can include lists having potential metabolites having substantially the same mass measurement, substantially the same retention time, substantially the same drift time, or combinations thereof. For example, a first tentative list can have potential metabolites having only substantially the same mass measurement (e.g., m/z only) and a second list having potential metabolites having substantially the same mass measurement and substantially the same retention time (e.g., m/z and RT). The number of lists can be at least 2, 3, 4, 5, 6, 7, 8, 9, 10, 15, 20, 25, 50 or about 100 tentative lists. These values can be used to define a range, such as about 2 to about 10 lists.

The two or more tentative metabolite identification lists can be compared with two or more known metabolic pathways. The comparison can use any statistical methodology capable of comparing two or more lists of potential metabolites with numerous metabolic pathways and identifying potential matches. For example, pathway analysis, which can include both enrichment analysis and pathway topological analysis, can be conducted using Metabolomics Pathway Analysis (MetPA) within Metaboanalyst Version 2.0. Metabolite enrichment analysis is a method designed to help metabolomics researchers identify and interpret patterns of metabolite concentration changes in a biologically meaningful way.

Figure 7A:
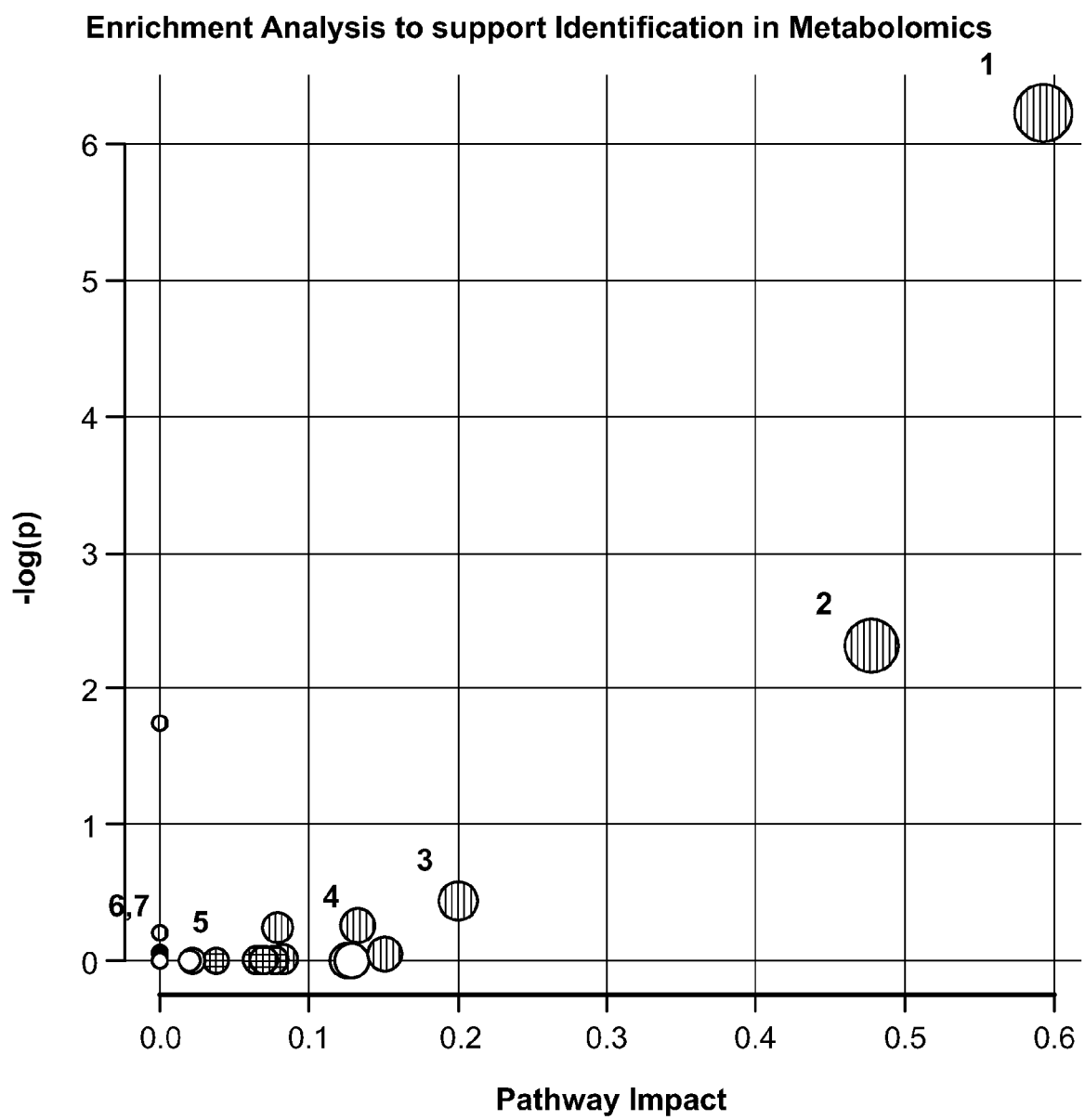
FIG. 7A shows a summary of a pathway analysis wherein matched pathways are shown as circles. The color and size of each circle can be based on the p value and pathway impact value, respectively.
Figure 7B:
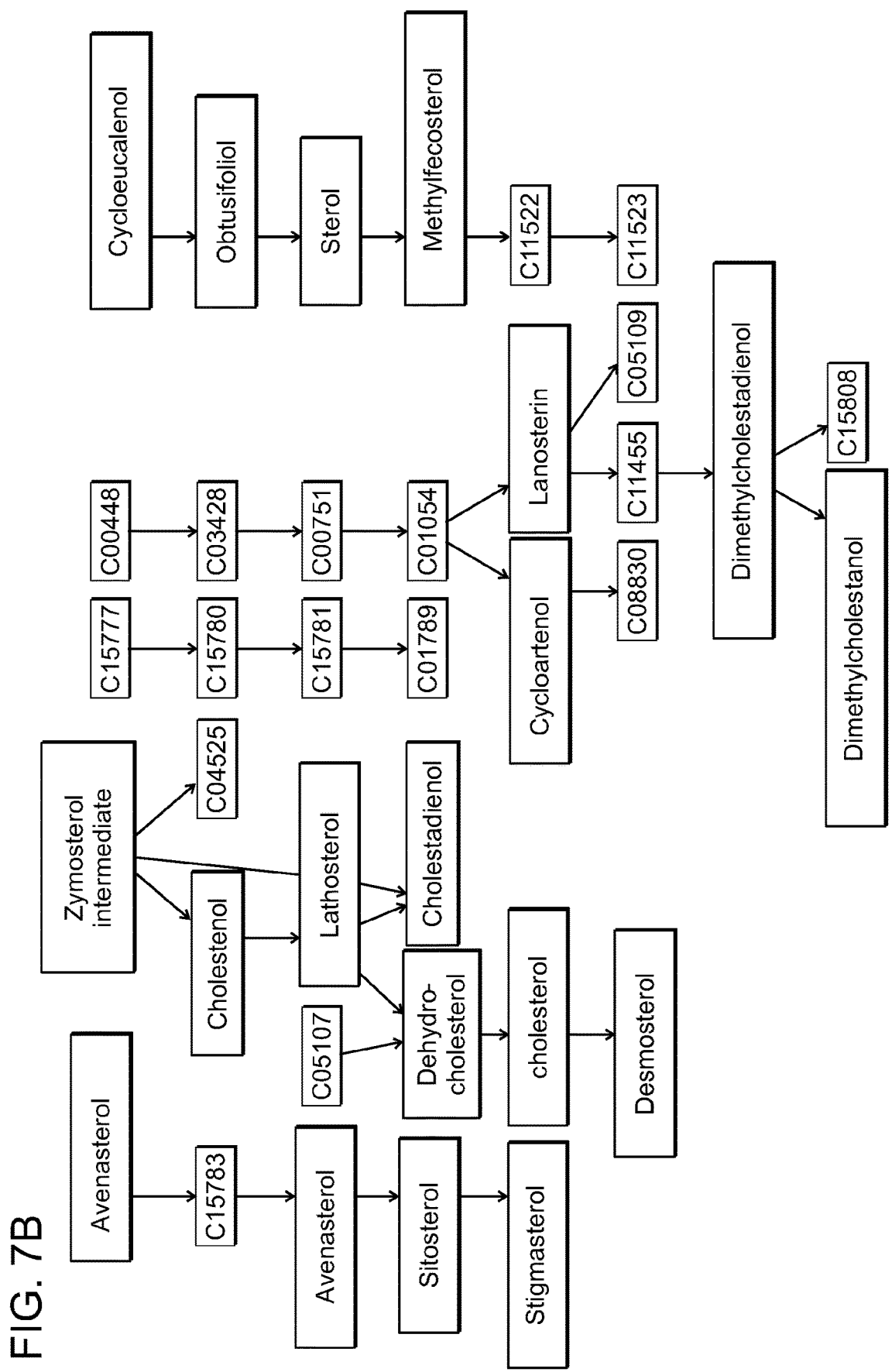
FIG. 7B shows a representation of the steroid biosynthetic pathway. The metabolites that accumulated in broccoli sprouts grown under conditions of continuous light are shown, as individually named, and compared with the metabolites in sprouts grown under conditions of continuous dark.
Figure 8B:
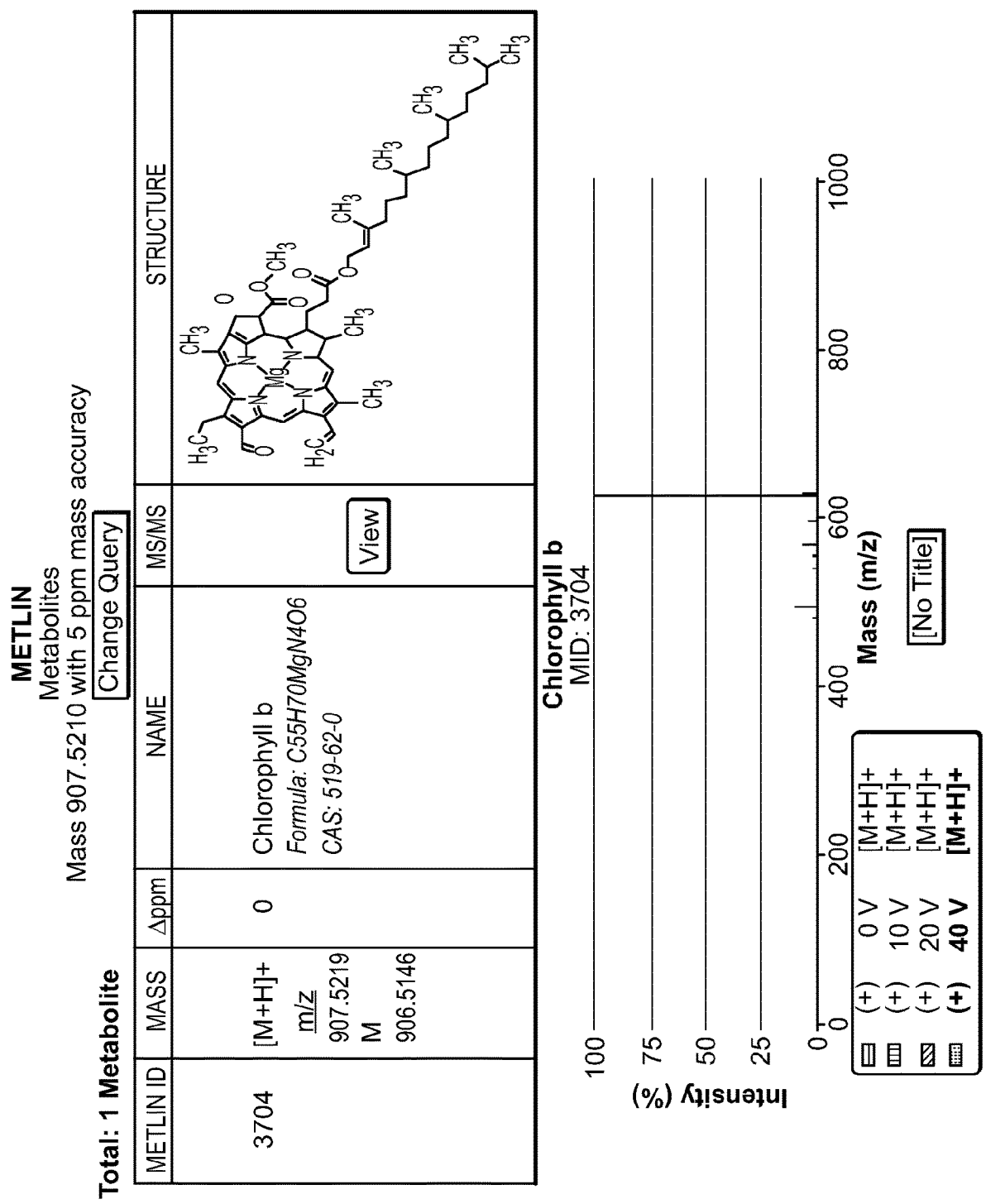
FIG. 8 shows a statistical identification of metabolic alterations and a review of the measurements using 3D montage and adducts deconvolution (FIG. 8A), and a search on local or online databases (e.g., METLIN) for structural identification (FIG. 8B). As described in Example 1, the database search led to a putative structure of a chlorophyll b, which was detected only in broccoli sprouts grown in light conditions.

The tentative metabolite identification lists can be compared to known pathways that appear in the KEGG pathway library. The pathway analysis can be matched, as shown in FIG. 7, wherein the p value, the pathway impact value, or both are above a pre-determined threshold. A metabolic pathway can be identified as statistically more likely to include the two or more metabolites wherein the pathway analysis values indicate a match.

The identification of at least one metabolic pathway that is statistically more likely to include the two or more metabolites can also be evaluated by known statistical methodology. For example, the statistically more likely metabolic pathway can be a pathway or pathways having a p-value less than about 0.1, 0.09, 0.08, 0.07, 0.06, 0.05, 0.04, 0.03, 0.02 or about 0.01. In one embodiment, P<0.05 represents a limit for the significance of the data against random association.

Figure 4A:
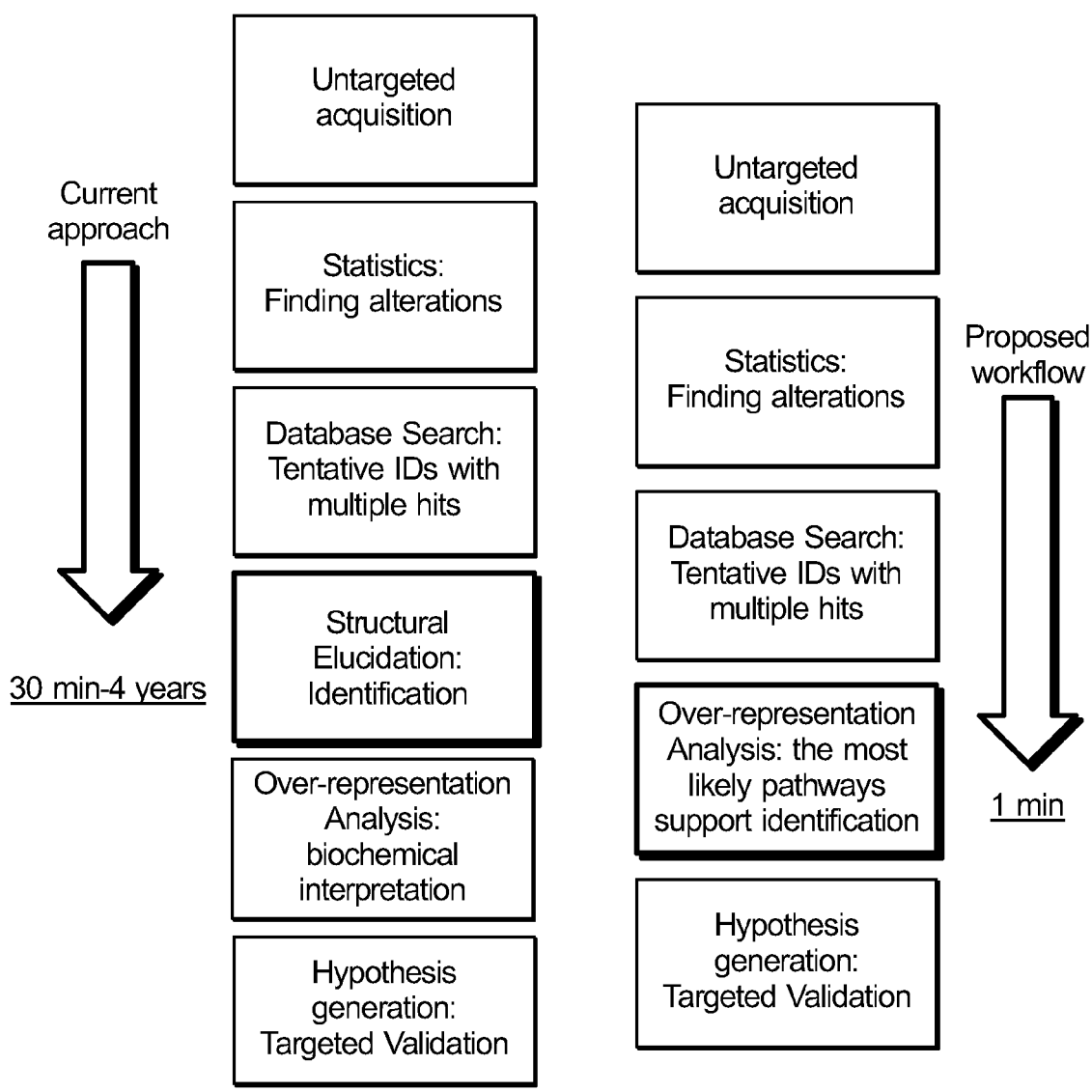
FIGS. 4A and 4B show exemplary overviews of the methodology of the present disclosure applied to untargeted metabolomics. The current approach shown on the left of each Figure requires at least some level of structural elucidation/identification prior to targeted validation of the pathway and metabolites. The present disclosure includes either enrichment analysis or over-representation after tentative identifications without the requirement of at least one structural elucidation prior to pathway and/or metabolite validation. The estimated time for successful validation using the current approach can be between about 30 minutes and 4 years. The estimated time for successful validation using the present disclosure can be greater reduced, and can be less than about 30 minutes, 20 minutes, 10 minutes, or about 1 minute.
Figure 4B:
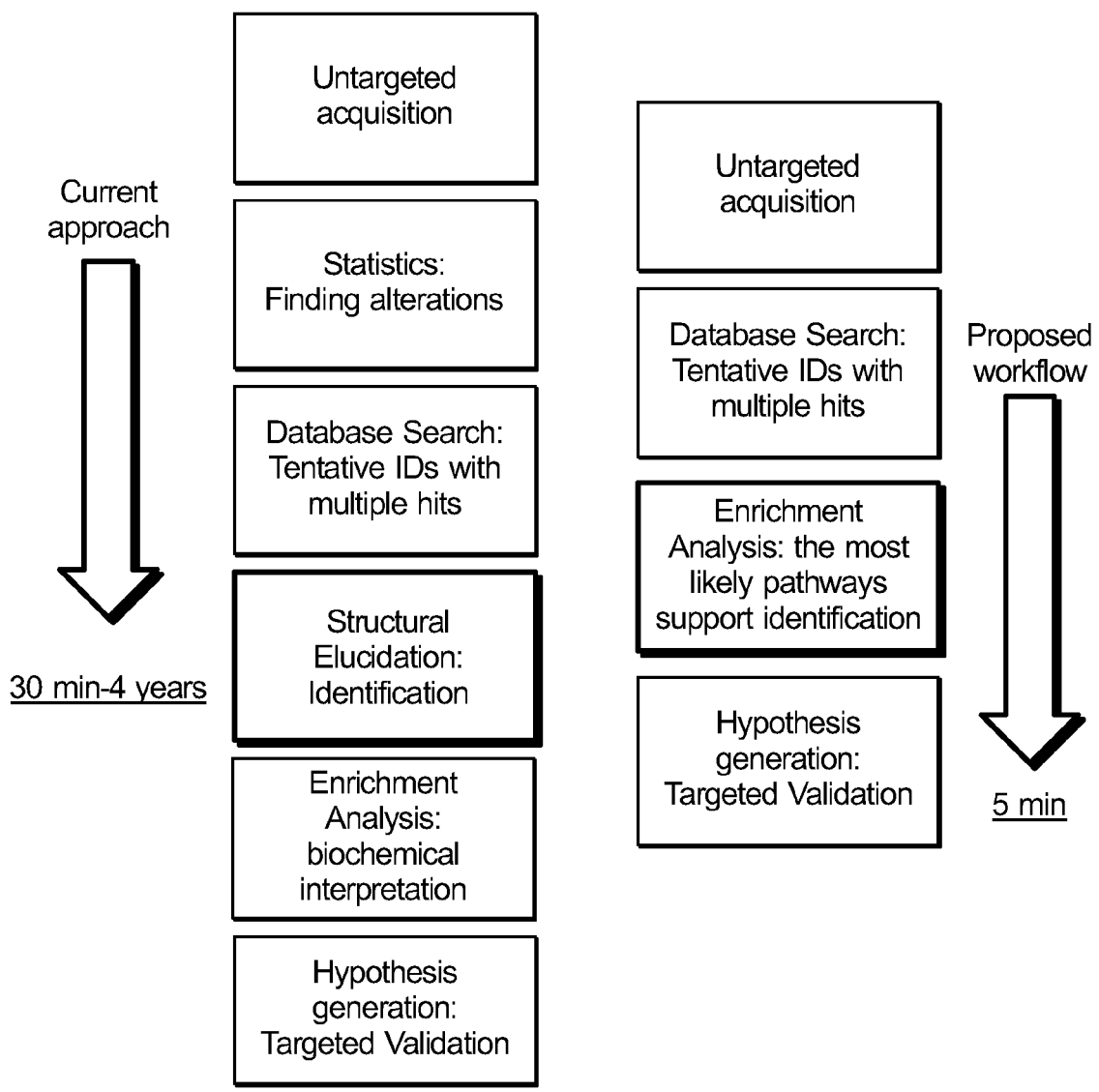

In one embodiment, the comparison can be performed without further analysis and structure elucidation of one or more of the metabolites. FIG. 4 shows the order of the methodology of the present disclosure. In the present disclosure, after the tentative identification lists are generated the enrichment analysis occurs to identify likely metabolic pathways. In the current approach, the next step is structural elucidation and enrichment analysis is done afterwards.

Once one or more metabolic pathways have been determined, the identity of at least one of the metabolites in a metabolic peak, wherein the metabolites in the peak have substantially the same mass measurement, substantially the same retention time, substantially the same drift time, or combinations thereof, and correspond to the metabolite peak, can be determined. The metabolic peak can be analyzed to positively identify at least one of the metabolites using the methodology and apparatus described herein.

The structural elucidation of the potential metabolite can be determined using chromatography, mass spectrometry and data-independent acquisition. For example, using a method that includes both high and energy fragmentation mass spectrum of a ion or potential metabolite can be used to cross-reference a set of peaks in the low energy fragmentation mass spectrum with a set of peaks in the high energy fragmentation mass spectrum that are substantially similar and determining a chemical structure of the metabolite. The high energy fragmentation mass spectrum and a low energy fragmentation mass spectrum of a ion can be generated using data independent methods, such as $MS^E$ or $HDMS^E$. See, e.g., U.S. Pat. Nos. 6,717,130 and 6,586,727, entire disclosures of both are incorporated by reference herein in their entirety.

Data independent acquisition involves the use of a collision cell that alternates low and high collision energy before MS detection. The low-energy spectra can contain ions primarily from unfragmented precursors, while the high-energy spectra can contain ions primarily from fragmented precursors. The alternating energy protocol can collect spectra from the same precursor in two modes, a low-energy mode and a high-energy mode.

Thus, the output of the instrument using data independent acquisition is an inventory, or list, of precursor and fragment ions, each ion can be described by its retention time, drift time, isolated/selected m/z, determined m/z, intensity, etc, or combinations thereof. The low-energy mode can produce a list of ions that contains primarily unfragmented precursor ions. The high-energy mode can produce a list of ions that contains primarily fragmented precursor ions. As described in U.S. Pat. Nos. 6,717,130 and 6,586,727, the parent-daughter peaks can be grouped upon these descriptions, e.g., retention time and/or drift time. These groupings can assist in structural elucidation.

In another embodiment, the present disclosure relates to a method of identifying a metabolic pathway containing two or more metabolites, including (i) receiving a sample containing metabolites, (ii) receiving a standard containing metabolites, (iii) analyzing the sample with a mass spectrometer system to generate sample metabolite peaks, wherein each sample metabolite peak has a signal intensity and at least a mass measurement, (iv) analyzing the standard with a mass spectrometer system to generate standard metabolite peaks, wherein each standard metabolite peak has a signal intensity and at least a mass measurement, (v) comparing the sample metabolite peaks and the standard metabolite peaks to identify one or more altered metabolite peaks having an intensity difference, (vi) generating a tentative metabolite identification list for at least two or more of the altered metabolite peaks, wherein each list comprising potential metabolites having substantially the same mass measurement, (vii) comparing the two or more tentative metabolite identification lists with two or more known metabolic pathways, and (viii) identifying at least one metabolic pathway that is statistically more likely to include the two or more metabolites.

The received sample can be any sample containing metabolites, such as a biological sample. The sample can be neat, filtered or processed. The sample can be a complex sample containing over hundreds or over thousands of different metabolites. The sample can contain one or more metabolites that are related by a metabolic pathway, e.g., both are contained in or part of the metabolic pathway. The sample can be exposed to a stimulus, etc. The sample can be tested against a standard that is not exposed to the stimulus, etc. The sample can contain one or more metabolites that are affected or altered by the stimulus. The standard can contain metabolites that are not affected or altered by the stimulus.

The sample and the standard can be analyzed by a mass spectrometer system as described herein. The mass spectrometer system can provide a mass measurement, or an exact mass measurement, of components of the sample and standard. The mass spectrometer system can also contain a separation component, such as a chromatographic separation, an ion mobility separation, or both coupled, up stream, of the mass spectrometer.

The mass spectrometer system, or chromatography-mass spectrometer system, or chromatography-ion mobility-mass spectrometer system can generate one or more peaks having a peak intensity, a mass measurement, a retention time, a drift time, or combinations thereof for each sample and standard tested. The sample metabolite peak data and the standard metabolite peak data can be compared to identify one or more altered metabolite peaks. The altered metabolite peaks can be peaks having an intensity that differs by greater than about 1%, 2, 3, 4, 5, 6, 7, 8, 9, 10, 15 or about 20%. These values can also define a range, such as about 2 to about 5%.

The data sets can also be compared or analyzed using multivariate statistical tools and chemometric analyses. The multivariate statistical analyses can include PCA, independent component analysis (ICA), correlation analysis, orthogonal partial least squares (O-PLS), PLA-DA, ANOVA analysis or combinations thereof. In addition, non-linear methods also known as kernel methods, such as support vector machines (SVM) and Kernel PLS can be used. For example, the altered metabolite peaks can have a P<0.05. A listing of analysis techniques are listed below:

| Analysis Techniques |
| --- |
| Univariate Analysis |
| Multivariate Analysis |
| Principal Component Analysis (PCA) |
| Linear Discriminant Analysis (LDA) |
| Maximum Margin Criteria (MMC) |
| Library Based Analysis |
| Soft Independent Modelling Of Class Analogy (SIMCA) |
| Factor Analysis (FA) |
| Recursive Partitioning (Decision Trees) |
| Random Forests |
| Independent Component Analysis (ICA) |
| Partial Least Squares Discriminant Analysis (PLS-DA) |
| Orthogonal (Partial Least Squares) Projections To Latent Structures (OPLS) |
| OPLS Discriminant Analysis (OPLS-DA) |
| Support Vector Machines (SVM) |
| (Artificial) Neural Networks |
| Multilayer Perceptron |
| Radial Basis Function (RBF) Networks |
| Bayesian Analysis |
| Cluster Analysis |
| Kernelized Methods |
| Subspace Discriminant Analysis |

PCA is mathematically defined as an orthogonal linear transformation that transforms the data to a new coordinate system such that the greatest variance by any projection of the data comes to lie on the first coordinate (called the first principal component), the second greatest variance on the second coordinate, and so on. PCA can be used for dimensionality reduction in a data set by retaining those characteristics of the data set that contribute most to its variance, by keeping lower-order principal components and ignoring higher-order ones. Such low-order components often contain the "most important" aspects of the data. The common compound peaks for any given sample can be segregated into distinguishing clusters using principle component analysis (PCA).

A tentative metabolite identification list for each altered metabolite peak can be generated by searching known databases against the accurate mass measurement. Each list having potential metabolites can have substantially the same mass measurement. The known databases can be in-house databases or can be publically available databases, such as LIPIDMAPS, HMDB and METLIN. The tentative metabolite identification lists for each altered metabolite peak can also be generated by searching known databases against the fragmentation pattern, retention time, collision cross sections, or combinations thereof. Each list having potential metabolites can have substantially the same fragmentation pattern, retention time, collision cross sections, or combinations thereof.

In addition to pathway analysis using enrichment, the at least one metabolic pathway can be identified or confirmed using an over-representation analysis tool. An over-representation analysis tool can be used to test if a particular group of compounds is represented more than expected by chance within the user uploaded compound list. In the context of pathway analysis, what is tested is if compounds involved in a particular pathway are enriched compared by random hits. The methodology of the present disclosure can be used to identify metabolites within the same, or similar pathways, that may only have subtle, but significant, changes. Identifying these metabolites can be done by re-analyzing the already processed datasets, and re-processing the datasets for peak-picking and extraction of the intensity values related to known metabolites present in the highlighted pathways.

For example, over-representation analysis can be performed on a list of metabolite identifiers to analyses whether the list is significantly associated with a particular pathway or set of pathways (e.g., localized to certain pathways or classifications, instead of randomly scattered throughout the whole set of possible pathways). A list of identifiers of interest can be selected or identified which are a sub-set of all the metabolites measured, such as those metabolites significantly different between experimental conditions. The test can be relatively quick, as it can be used for only testing a sub-list of metabolites. However, it can rely on having selected a sub-set appropriately, and all metabolites on the list are treated as equally important by the test (which might not be the case if they are actually altered by very different amounts, for example).

Enrichment analysis, for comparison, is most often done on the full metabolite feature set, along with an expression measure for each metabolite reflecting its difference between two states (e.g., the log fold-ratio between two conditions' mean normalized abundance for each compound, with up-regulation expressed as a positive value and down-regulation expressed as a negative one). This analysis can consider these values for all metabolites, but can test for trends in the metabolites including each pathway, looking for a significant coordinated effect across all the relevant ratios to test whether the pathway is being up- or down-regulated in a manner that is unlikely to be accounted for by random chance.

The Wilcoxon test is a rank-based analysis, using the ranking of the enrichment ratios over the set rather than their absolute values. This test is a more hypothesis-free approach, in that metabolites of interested do not need to be preselected, and also the relative extent of between-group differences can be taken into account for every metabolite. However, it is a more complex analysis and may take longer, because all metabolites are being considered. In one embodiment, over-representation analysis looks at whether a subset of metabolites that have been separated out associate significantly with certain pathways, whereas enrichment analysis takes differential data from every measured metabolite and looks for pathways displaying significantly coordinated shifts in those values. See, e.g., Kamburov et al., 2011: "Integrated pathway-level analysis of transcriptomics and metabolomics data with IMPaLA." Bioinformatics 27: 2917-8. DOI: 10.1093/bioinformatics/btr499; Afsari et al., 2014: "Learning Dysregulated Pathways in Cancers from Differential Variability Analysis." Cancer Informatics 13 (Suppl 5):61-7. DOI: 10.4137/CIN.S14066. Both references are incorporated herein by reference in their entirety.

In another embodiment, a post analysis data-dependent processing can extract intensity information of not originally extracted features based on pre-set pathways analysis and potential their phase I and phase II metabolites. For example, if the enrichment or over-representation pathway analysis pointed to the arachidonic acid metabolism being altered, and multiple, e.g, five, metabolites are enriched in this pathway based on the data deriving from first pass processing, an informatic solution can reprocess the data based on all the known metabolites present in that pathway, extracting features than may not have been detected during first pass processing.

After one or more metabolic pathways have been determined, one or more of the potential metabolites can be identified by comparison of the mass measurement, retention time, drift time, collision cross sections, fragmentation pattern, or combinations thereof.

The disclosures of all cited references including publications, patents, and patent applications are expressly incorporated herein by reference in their entirety.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention is further defined in the following Examples. It should be understood that these Examples, while indicating preferred embodiments of the invention, are given by way of illustration only.

EXAMPLES

Example 1

The methodology of the present disclosure was used to identify major molecular alterations in a biological sample as a result of exposure to a stimulus. An untargeted metabolomics analysis was performed with broccoli sprouts following light exposure. The untargeted metabolomics reveals predominant alterations in lipid metabolism as a result of light exposure.

Overview:

The consumption of vegetables belonging to the family Brassicaceae (e.g., broccoli and cauliflower) is linked to a reduced incidence of cancer and cardiovascular diseases. The molecular composition of such plants is strongly affected by growing conditions. An unbiased metabolomics approach was developed to investigate the effect of light and dark exposure on the metabolome of broccoli sprouts, which are known to be particularly enriched in bioactive metabolites. Broccoli seeds were germinated and grown hydroponically for five days in total darkness or with a light/dark photoperiod (16 hours light/8 hours dark cycle). An UHPLC system coupled to an ion-mobility, time-of-flight mass spectrometer was used to profile the large array of metabolites present in the sprouts. Differences at the metabolite level between groups were analyzed using multivariate statistical analyses, including principal component analysis and correlation analysis. Altered metabolites were identified by searching publicly available and in-house databases. Metabolite pathway analyses were used to support the identification of subtle but significant changes among groups of related metabolites that may have gone unnoticed with conventional approaches. The chlorophyll pathway was activated by light exposure. In addition, light exposure activated the biosynthesis and metabolism of sterol lipids, prenol lipids, and polyunsaturated lipids, which are essential for the photosynthetic machinery. Light exposure also increased the levels of polyketides, including flavonoids, and oxylipins, which play essential roles in the plant's developmental processes and defense mechanism against herbivores. The methodology and apparatus of the present disclosure can identify the significant contribution and effects of light exposure to the ultimate metabolic phenotype, which might ultimately affect the cellular physiology and nutritional value of broccoli sprouts.

Introduction:

The Brassicaceae, a family of widely consumed plants, includes broccoli, cabbage, kale, Brussels sprouts, and many other vegetables. The known healthful effects of ingesting these vegetables include a lower risk of developing cancer and cardiovascular diseases. [1-4] Yet the extent to which the effects of various growth conditions, particularly light exposure, affect the vegetables' metabolism, and hence their nutritional value, remains incompletely characterized.

Young broccoli plants are especially enriched in antioxidant and chemoprotective metabolites, with levels several times greater than those of mature plants. [5] The molecular composition of broccoli sprouts reflects both genetic and environmental components. For that reason, comprehensive metabolite profiles can more completely describe the vegetables' ultimate nutritional value than can genomics approaches (FIG. 1A). Metabolomics is a modern analytical approach that uses state-of-the-art instrumentation, such as mass spectrometry, to characterize the molecular composition of biological samples. [6] To date, metabolomics investigations of broccoli sprouts have mainly focused on "targeted metabolomics" approaches, thus focusing on analyzing selected molecular classes, including glucosinolates, isothiocyanates and anthocyanins. [1, 7-14]

A complementary approach, "untargeted metabolomics," can screen the entire metabolite content of biological samples. Such an unbiased approach can be used for characterizing the molecular phenotype of individual samples or for comparing profiles of metabolites among different sample groups. Recent technological advances in the field of mass spectrometry allow both qualitative and quantitative analysis to be performed on thousands of metabolites in a single analysis. [6, 15-18]

When germinated in the dark, in an attempt to reach a source of light, the sprouts undergo a developmental program called skotomorphogenesis characterized by great cell expansion driven by water uptake and consumption of the metabolic reserve accumulated into the seed. Therefore dark grown sprouts can be considered to have a minimal metabolic complexity. On the contrary, light exposure during germination induces the photomorphogenic program leading to the establishment of autotrophy. Due to the conversion of light energy into chemical energy and to the oxidative stress associated to the photosynthesis, light grown sprouts are characterized by a high metabolic activity.

Untargeted metabolomics was used to investigate the molecular changes occurring in the complete set of metabolites of broccoli sprouts grown under conditions of light or dark. By comparing, in an unbiased fashion, the molecular information of such extreme growth conditions, major biochemical pathways and corresponding metabolites affected by light exposure were determined.

Materials and Methods:

Broccoli seeds, (*Brassica oleracea* L. var. *botrytis* subvar. *cymosa*), purchased from SUBA&UNICO (Longiano, FC, Italy), were germinated in the Vitaseed sprouter germination cylinder (Vitaseed AG, Switzerland) inside the phytotron and kept until harvesting in the germination cylinder. The seeds were grown hydroponically for five days at 21° C. in a plant-growth chamber (Weiss Gallenkamp, Loughborough, United Kingdom). The chamber was equipped with fluorescent tubes, PHILIPS Master TL-D 36W/840, cool-white. The tubes provided a photosynthetic photon flux density of 110 mmol $M^{-2}$ $s^{-1}$. Two light regimes were adopted: (1) dark; and (2) light (16 hours light/8 hours dark cycle), n=3 per group.

Sample Preparation:

Sprout samples, collected from the germination cylinder, were immediately frozen in liquid nitrogen and stored at −80° C. Metabolite extraction was conducted using known techniques. Briefly, frozen sprouts were ground to a fine powder in a Waring blender, which was cooled with liquid nitrogen. Each sample of broccoli sprouts was extracted with methanol (sample-to-solvent ratio=1:25 w/v) at 70° C. for 30 min while vortex mixing. The samples were successively centrifuged (4000 rpm, 30 min, 4° C.), the supernatants collected, and the solvent completely removed, under vacuum at 40° C., using a rotary evaporator. The dried samples were dissolved in methanol and filtered through 0.20-μm syringe PVDF filters before MS analysis.

Liquid-Chromatography (UHPLC) Conditions:

Hydrophobic metabolites were separated using an ACQUITY® UPLC system (Waters Corporation, Milford, Mass., USA) equipped with a CSH C18 column (2.1×100 mm ID, 1.7 μm). A gradient elution was performed. Mobile phase A was composed of 60:40 (v/v) 10 mM ammonium formate in acetonitrile/water. Mobile phase B was composed of 10 mM formate in isopropanol/acetonitrile. The elution gradient was as follows: 0-2 min, 40-43% B; 2.0-2.1 min, 43-50% B; 2.1-12 min, 50-54% B; 12-12.1 min, 54-70% B; 12.1-18 min, 70-99% B; 18-18.1 min, 99-40% B; 18.1-20 min, 40% B. The column was kept at 55° C.; the flow rate was 0.4 mL/min and the injection volume 5 μL.

Polar metabolites were separated using a UHPLC system (ACQUITY® UPLC system Waters Corporation, Milford, Mass., USA) fitted with a BEH HILIC column (2.1×100 mm ID, 1.7 μm). Mobile phase A was composed of 95:5 acetonitrile/water (v/v) containing 10 mM ammonium acetate (pH 8.0). Mobile phase B was composed of 50:50 acetonitrile/water (v/v) containing 10 mM ammonium acetate (pH 8.0). A 10-minute linear gradient, from 100% to 80% A, with a 3-minute re-equilibration time, was applied. The column was kept at 30° C.; the flow rate was 0.5 mL/min and the injection volume 5 μL.

Ms Conditions:

MS analyses were performed on an ion-mobility-enabled quadrupole, time-of-flight (QTof) mass spectrometer (Synapt® G2-S, Waters Corporation, Milford, Mass., USA). Data were acquired, from 50 m/z to 1, 500 m/z in both positive and negative electrospray ionization modes. The mass spectrometer was operated under the following conditions: capillary voltage 2.0 KV (+ve) and 1.0 KV (−ve); cone voltage 30 V; transfer CE ramp 20 to 50 V; source temperature 120° C.; desolvation temperature 550° C.; cone gas 50 L/h; MS gas nitrogen. Data were collected in two channels: low collision energy (6.0 V), for the molecular ions, and high collision energy (15-40 V), for product ions. The ion-mobility gas was nitrogen, and the T-wave velocity and height were 900 m/s and 40 V, respectively.

Data Processing and Analysis:

Data processing and analysis was conducted using Progenesis QI Informatics (Nonlinear Dynamics, Newcastle, UK). [19] Each UHPLC-MS run was imported as an ion-intensity map, including m/z and retention time. These ion maps were then aligned in the retention-time direction. From the aligned runs, an aggregate run representing the compounds in all samples was used for peak picking. This aggregate was then compared with all runs, so that the same ions are detected in every run. Isotope and adduct deconvolution was applied, to reduce the number of features detected. Data were normalized according to total ion intensity. A combination of analysis of the variance (ANOVA) and multivariate statistics, including principal component analysis (PCA) and partial, least-squares discriminant analysis (PLS-DA), identified metabolites most responsible for differences between sample groups. Metabolites were identified by database searches against their accurate masses using publicly available databases, including LIPIDMAPS [20], HMDB [21], and METLIN [22], as well as by fragmentation patterns, retention times and collision cross sections, when available. Pathway analysis, which consisted of enrichment analysis and pathway topological analysis, were conducted using Metabolomics Pathway Analysis (MetPA) within MetaboAnalyst. [23] Additional pathway over-representation and enrichment analyses with metabolite data were conducted using Metabolite Pathway Identification via coupling of global metabolite Network structure and metabolomic profile (MPINet) [24] and Integrated Molecular Pathway Level Analysis (IMPaLA) [25].

Results and Discussion

To maximize the separation of the wide range of metabolites present in the broccoli sprouts, a combination of UHPLC and ion-mobility separations were used. [19, 26, 27] The analysis provided a multidimensional metabolite fingerprint, which represented a "snapshot" of the metabolite inventory for each sample analyzed (FIG. 1). FIG. 1 shows an overview of a test method screen a biological network.

FIG. 1 shows that different classes of compounds can be screened in a biological sample including all of the metabolites. Metabolites can derive from both the generic imprint and from the environment (e.g., light exposure). Complex samples can contain thousands of metabolites and have a wide range of chemical complexity and concentration. The profiling of the entire set of metabolites (i.e., the metabolome) defines the molecular phenotype of the biological system.

The system for untargeted metabolomics can include a UHPLC system coupled with an ion mobility-enabled QTof MS. After UHPLC separation, the metabolites can be further separated in another dimension using ion-mobility before MS detection. This combination of UHPLC and ion mobility can provide increased peak capacity and specificity in the quantification and identification process.

Differences at the metabolite level between groups were analyzed using multivariate statistical tools, including PCA and correlation analyses (FIG. 5). The metabolites that contributed most to the variance between groups were isolated using PLS-DA and ANOVA (FIG. 5).

Figure 5B:
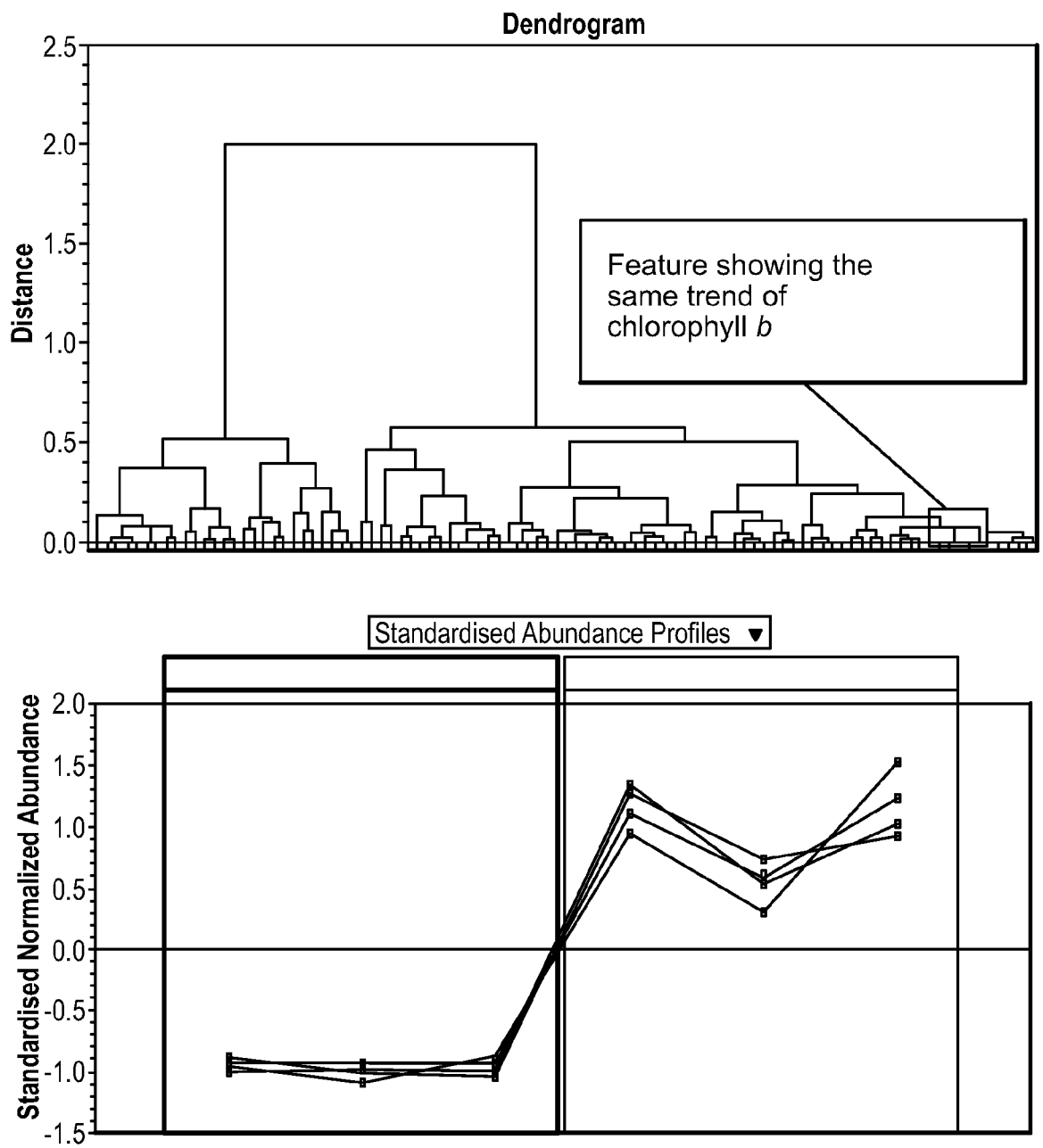
FIG. 5B shows a correlation analysis that can identify similar patterns of alterations among metabolites. The variance and identification of similar patterns was performed using techniques common to metabolomics, such as using Progenesis QI (Nonlinear dynamics, Newcastle UK). As described in Example 1, a metabolite with m/z 907.5210 was increased in the light exposed samples. The metabolite was then identified as chlorophyll b.

FIG. 5 shows an exemplary statistical analysis of metabolite peaks. FIG. 5A shows a multivariate statistical analysis of a UHPLC/HDMS$^E$ test data. The separated samples can be segregated into clusters using PCA. (5A, top). The metabolites that contribute most to the variance among groups can be isolated using PLS-DA (5A, bottom). FIG. 5B shows a correlation analyses that can identify similar patterns of alterations among metabolites. As described in Example 1, a metabolite with m/z 907.5210 was increased in the light exposed samples. The metabolite was then identified as chlorophyll b.

Metabolite identification is a useful step for converting data into meaningful, biological results. In a typical MS-based metabolomics experiment, features of interest are searched against databases that list physicochemical properties descriptive of each metabolite (e.g., accurate mass). Initial searches performed using publicly available and in-house databases led to more than 700 tentative identifications of metabolites that accumulated in the broccoli sprouts exposed to light. To identify and determine the structure (e.g., structural elucidation) of the metabolites, data-independent acquisition was coupled with ion-mobility separation in a high definition $MS^E$ ($HDMS^E$) mode of operation. [19, 26-31] Because many of the molecules in the complex matrix co-eluted, the incorporation of ion mobility allowed the separation of ions before fragmentation which produced a cleaner, tandem-MS, product-ion spectra that facilitated metabolite identification (FIG. 6). [19, 28-32]

Figure 6A:
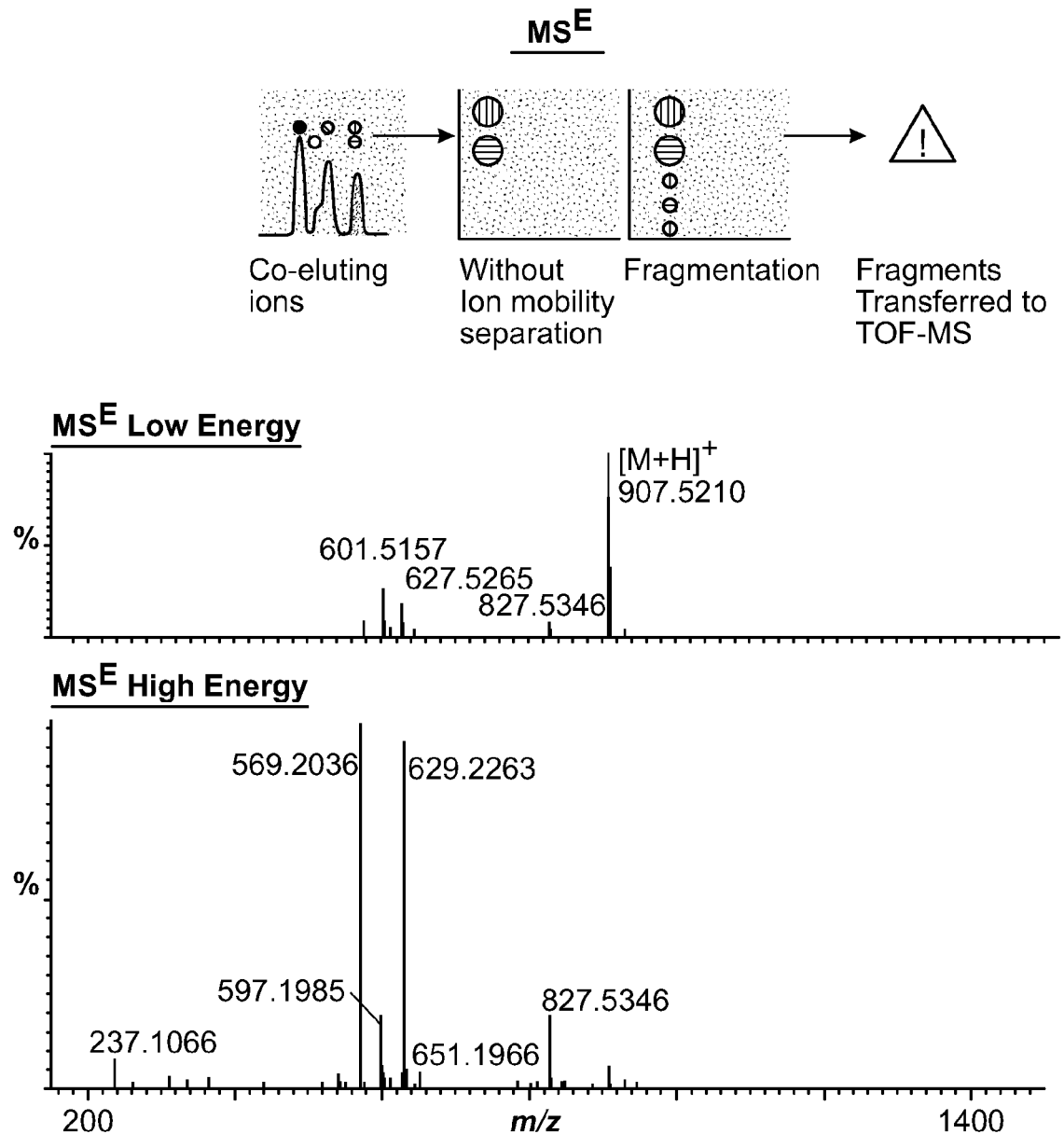
FIG. 6A shows the system without ion mobility separation (e.g., MS$^E$).

FIG. 6 shows an exemplary analysis using a chromatographic separation and mass spectrometry with and without an ion mobility separation. FIG. 6A shows the system without ion mobility separation (e.g., $MS^E$). FIG. 6B shows the system with ion mobility separation (e.g., $HDMS^E$). Both systems allow for the acquisition of both precursors and fragment spectra information with one single chromatographic run. The application of high collision energy in the transfer collision cell can allow the precursor molecules to be broken down into their constituent parts (product ions), and can allow determination of the original structure. The identification of metabolites in complex mixtures, such as the identification of the chlorophyll b structure, can be aided by the observation of characteristic fragments generated with high energy after ion-mobility separation. The addition of an ion-mobility separation of co-eluting precursor metabolites can produce a cleaner and less complex product ion spectra. As described in Example 1, the identification of chlorophyll b by searching against databases was simplified using a chromatographic separation and mass spectrometry with an ion mobility separation.

Despite the cleaner spectra, it can still be difficult, impractical or impossible to verify the identification for each potential metabolites, including isomers, isobars and other unlikely plant metabolites. As highlighted in FIG. 6, each peak can still present numerous potential metabolites. The top peak identified in FIG. 6 is shown to have 25 potential metabolite hits, or 25 tentative identifications. These tentative identifications were compared with 87 pathways that appear in the Kyoto Encyclopedia of Genes and Genomes (KEGG) pathway library of *Arabidopsis thaliana* (thale cress), a member of the same family, Brassicaceae, as the broccoli sprouts (FIG. 7) [23]. By testing whether a set of metabolites is enriched in a particular pathway, compared with random hits, metabolite identification was achieved in a more efficient manner, in less time and using less resources than using prior methodology. Because metabolite changes are interconnected and occur in a coordinated fashion in biology, finding multiple metabolite hits within a particular biochemical pathway increased the probability that the identification is correct. In one embodiment, the increased probability can be measured using an over-representation analysis, such as a Fisher's Exact test or a Hypergeometric Test.

Over-representation tools were also used, including MPINet and IMPaLA, to further support the validity of the initial metabolite determinations. [24, 25] These complementary metabolomic pathway analyses were used to identify subtle, but significant changes, among groups of related metabolites that may have gone unnoticed with conventional approaches (FIG. 7). Over-representation tools are similar to enrichment analyses and are based on similar principles (e.g., how many of the metabolites are represented in a particular metabolic pathway). In one embodiment, the intensities and/or concentrations of metabolites (e.g., precursors and metabolites) can be used to determine a flux (e.g., direction) of the pathway alterations. For example, if a precursor decreases and a metabolite increases, an association can be made that the pathway is moving forward in a particular direction.

In one embodiment, machine learning algorithms analysis can be used to learn patterns and networks of metabolites across multiple experiments, independently from inputs of known biochemical pathways. By re-applying the newly acquired network knowledge in a series of separate experiments, patterns of changes can be derived among all the potential hits, facilitating metabolite or lipid identification.

In another embodiment, genetics, genomics, transcriptomics, peptidomics and proteomics information can be integrated or fused with metabolomics and lipidomics data, and Bayesian network(s) can be used to facilitate identifications as described herein.

Using the analysis of the present disclosure, the alterations in chlorophyll biosynthesis (FIG. 7) were confirmed. Also observed was the accumulation of phytosterols, prenol lipids, carotenoids and polyunsaturated fatty acids-containing lipids in broccoli sprouts grown under conditions of light/dark cycle, compared with conditions of continuous dark (FIG. 7). Sterol lipids are known to play key roles in the growth and development of plants and to contribute to controlling the expression of genes linked to photosynthesis [33, 34]. The increase in carotenoid species is known to help plants absorb light energy and to protect chlorophyll against photooxidative stress [35, 36]. The increase in the desaturation of fatty acids has been proposed as an adaptive response to shifts in light intensity [37, 38]. The remodeling of membrane fluidity might, indeed, affect lipid-protein interactions, including the self-assembly of active chlorophyll-protein complexes for photosynthetic apparatus [37, 38]. Thus the concomitant activation of the steroid, chlorophyll, carotenoid, and polyunsaturated fatty acid (PUFA) pathways by light exposure can work synergistically for the engagement of the photosynthetic machinery. Notably, carotenoids and PUFA are both essential to human health, and they are absorbed through diet [39-42]. Consumption of phytosterols affects the endogenous sterol lipid metabolism and has been linked to decreased cardiovascular diseases and cancer [43-45].

The time to successfully identify at least one of the pathways included the sample preparation time, analysis time and processing time. At least one pathway was identified shortly after the processing of the data, and within the same day of the preparation and analysis. It is estimated that the identification, without the present disclosure, would have taking weeks or months to identify at least one pathway.

It was also found that light exposure increased the levels of various polar metabolites belonging to the category of polyketides, including flavonoids. These molecules, known to possess strong antioxidant properties, have been associated with health-promoting benefits [46-48]. It also was found that the levels of polyketides were affected by environmental conditions including temperature and light conditions [5, 7, 11, 49-60]. These observed changes in phytochemical composition following light exposure are responsible not only for the organoleptic properties, like flavors and aromas, of the broccoli sprouts, but also for their nutritional value and health properties [61].

Finally, an increase in the metabolism of PUFA (FIG. 7) was identified. Bioactive lipid mediators derived from both the enzymatic and non-enzymatic oxygenation of PUFA are known to play key roles in the life cycle of plants, including the regulation of the final maturation processes and the release of pollen [62]. A significant increase was found in PUFA-derived hexenal species in the broccoli sprouts grown under conditions of light/dark cycle, compared with conditions of continuous dark [63].

The metabolomic methodology of the present disclosure utilized (i) known metabolites currently present in databases and/or identified using current experimental technology, (ii) known metabolic networks and biochemical pathways, and (iii) subclass differentiation for select classes of metabolites or lipids that have independent metabolism and biological activity. The utility of the methodology will increase as these databases expand. Using the untargeted metabolomic methodology of the present disclosure, a set of significant and coordinated alterations in major metabolic pathways activated by light exposure during growth in broccoli sprouts was determined in an unbiased fashion.

CONCLUSIONS

In this Example, an unbiased metabolomics methodology was developed and applied to determine the metabolic phenotypes of broccoli sprouts grown under conditions of light/dark cycle, compared with conditions of complete darkness. The Example indicated the activation and coordination of specific metabolic pathways in broccoli sprouts exposed to light, which might ultimately affect their cellular physiology and nutritional value. In particular, a predominant role for lipid metabolism in the light-induced molecular remodeling of broccoli sprouts was highlighted. Exposure to light during growth affected the chlorophyll metabolism as well as major lipid biochemical pathways essential for engaging the photosynthetic machinery. These pathways include the steroid, carotenoid, and PUFA metabolism. It was also observed that light exposure induced changes in the levels of polyketides, including flavonoids and oxylipins, which are related to plant growth and maturation and, potentially, their defense mechanisms against herbivores and abiotic stresses. Major alterations in the diterpenoid metabolism and indole alkaloid biosynthesis as consequence of light exposure in broccoli sprouts was also observed. These finding show that the impact of an environmental stimuli on the overall plant biochemical pathway(s) can be efficiently identified using the methodology of the present disclosure.

REFERENCES

1. Cartea, M. E.; Velasco, P., Glucosinolates in *Brassica* foods: bioavailability in food and significance for human health. Phytochemistry reviews 2008, 7, (2), 213-229.
2. Traka, M.; Mithen, R., Glucosinolates, isothiocyanates and human health. Phytochemistry Reviews 2009, 8, (1), 269-282.
3. Verkerk, R.; Schreiner, M.; Krumbein, A.; Ciska, E.; Holst, B.; Rowland, I.; De Schrijver, R.; Hansen, M.; Gerhäuser, C.; Mithen, R., Glucosinolates in *Brassica* vegetables: the influence of the food supply chain on intake, bioavailability and human health. Molecular nutrition & food research 2009, 53, (S2), S219-S219.
4. Armah, C. N.; Traka, M. H.; Dainty, J. R.; Defernez, M.; Janssens, A.; Leung, W.; Doleman, J. F.; Potter, J. F.; Mithen, R. F., A diet rich in high-glucoraphanin broccoli interacts with genotype to reduce discordance in plasma metabolite profiles by modulating mitochondrial function. The American journal of clinical nutrition 2013, 98, (3), 712-722.
5. Pérez-Balibrea, S.; Moreno, D. A.; García-Viguera, C., Influence of light on health-promoting phytochemicals of broccoli sprouts. Journal of the Science of Food and Agriculture 2008, 88, (5), 904-910.
6. Astarita, G.; Langridge, J., An emerging role for metabolomics in nutrition science. J Nutrigenet Nutrigenomics 2013, 6, (4-5), 181-200.
7. Maldini, M.; Baima, S.; Morelli, G.; Scaccini, C.; Natella, F., A liquid chromatography-mass spectrometry approach to study "glucosinoloma" in broccoli sprouts. Journal of Mass Spectrometry 2012, 47, (9), 1198-1206.
8. Aires, A.; Rosa, E.; Carvalho, R., Effect of nitrogen and sulfur fertilization on glucosinolates in the leaves and roots of broccoli sprouts (*Brassica oleracea* var. *italica*). Journal of the Science of Food and Agriculture 2006, 86, (10), 1512-1516.
9. Velasco, P.; Francisco, M.; Moreno, D. A.; Ferreres, F.; García-Viguera, C.; Cartea, M. E., Phytochemical fingerprinting of vegetable *Brassica oleracea* and *Brassica napus* by simultaneous identification of glucosinolates and phenolics. Phytochemical Analysis 2011, 22, (2), 144-152.
10. Park, W. T.; Kim, J. K.; Park, S.; Lee, S.-W.; Li, X.; Kim, Y. B.; Uddin, M. R.; Park, N. I.; Kim, S.-J.; Park, S. U., Metabolic profiling of glucosinolates, anthocyanins, carotenoids, and other secondary metabolites in kohlrabi (*Brassica oleracea* var. *gongylodes*). Journal of agricultural and food chemistry 2012, 60, (33), 8111-8116.
11. Guo, R.; Yuan, G.; Wang, Q., Effect of sucrose and mannitol on the accumulation of health-promoting compounds and the activity of metabolic enzymes in broccoli sprouts. Scientia Horticulturae 2011, 128, (3), 159-165.
12. Guzman, I.; Yousef, G. G.; Brown, A. F., Simultaneous extraction and quantitation of carotenoids, chlorophylls, and tocopherols in *brassica* vegetables. Journal of agricultural and food chemistry 2012, 60, (29), 7238-7244.
13. Sun, J.; Xiao, Z.; Lin, L.-z.; Lester, G. E.; Wang, Q.; Harnly, J. M.; Chen, P., Profiling Polyphenols in Five *Brassica* Species Microgreens by UHPLC-PDA-ESI/HRMS n. Journal of agricultural and food chemistry 2013, 61, (46), 10960-10970.
14. Ahmadiani, N.; Robbins, R. J.; Collins, T. M.; Giusti, M. M., Anthocyanins Contents, Profiles, and Color Characteristics of Red Cabbage Extracts from Different Cultivars and Maturity Stages. Journal of agricultural and food chemistry 2014, 62, (30), 7524-7531.
15. Quanbeck, S. M.; Brachova, L.; Campbell, A. A.; Guan, X.; Perera, A.; He, K.; Rhee, S. Y.; Bais, P.; Dickerson, J. A.; Dixon, P., Metabolomics as a hypothesis-generating functional genomics tool for the annotation of *Arabidopsis thaliana* genes of "unknown function". Frontiers in plant science 2012, 3.
16. Fiehn, O., Metabolomics—the link between genotypes and phenotypes. Plant molecular biology 2002, 48, (1-2), 155-171.
17. Martinis, J.; Kessler, F.; Glauser, G., A novel method for prenylquinone profiling in plant tissues by ultra-high pressure liquid chromatography-mass spectrometry. Plant Methods 2011, 7, (1), 23.
18. Eugeni Piller, L.; Besagni, C.; Ksas, B.; Rumeau, D.; Brehelin, C.; Glauser, G.; Kessler, F.; Havaux, M., Chloroplast lipid droplet type II NAD(P)H quinone oxidoreductase is essential for prenylquinone metabolism and vitamin K1 accumulation. Proc Natl Acad Sci USA 2011, 108, (34), 14354-9.
19. Paglia, G.; Williams, J. P.; Menikarachchi, L.; Thompson, J. W.; Tyldesley-Worster, R.; Halldorsson, S.; Rolfsson, O.; Moseley, A.; Grant, D.; Langridge, J.; Palsson, B. O.; Astarita, G., Ion mobility derived collision cross sections to support metabolomics applications. Anal Chem 2014, 86, (8), 3985-93.

20. Fahy, E.; Subramaniam, S.; Murphy, R. C.; Nishijima, M.; Raetz, C. R.; Shimizu, T.; Spener, F.; van Meer, G.; Wakelam, M. J.; Dennis, E. A., Update of the LIPID MAPS comprehensive classification system for lipids. Journal of lipid research 2009, 50, (Supplement), S9-S14.
21. Wishart, D. S.; Jewison, T.; Guo, A. C.; Wilson, M.; Knox, C.; Liu, Y.; Djoumbou, Y.; Mandal, R.; Aziat, F.; Dong, E.; Bouatra, S.; Sinelnikov, I.; Arndt, D.; Xia, J.; Liu, P.; Yallou, F.; Bjorndahl, T.; Perez-Pineiro, R.; Eisner, R.; Allen, F.; Neveu, V.; Greiner, R.; Scalbert, A., HMDB 3.0—The Human Metabolome Database in 2013. Nucleic Acids Res 2013, 41, (Database issue), D801-7.
22. Smith, C. A.; O'Maille, G.; Want, E. J.; Qin, C.; Trauger, S. A.; Brandon, T. R.; Custodio, D. E.; Abagyan, R.; Siuzdak, G., METLIN: a metabolite mass spectral database. Ther Drug Monit 2005, 27, (6), 747-51.
23. Xia, J.; Mandal, R.; Sinelnikov, I. V.; Broadhurst, D.; Wishart, D. S., MetaboAnalyst 2.0—a comprehensive server for metabolomic data analysis. Nucleic acids research 2012, 40, (W1), W127-W133.
24. Li, F.; Xu, Y.; Shang, D.; Yang, H.; Liu, W.; Han, J.; Sun, Z.; Yao, Q.; Zhang, C.; Ma, J.; Su, F.; Feng, L.; Shi, X.; Zhang, Y.; Li, J.; Gu, Q.; Li, X.; Li, C., MPINet: metabolite pathway identification via coupling of global metabolite network structure and metabolomic profile. Biomed Res Int 2014, 2014, 325697.
25. Cavill, R.; Kamburov, A.; Ellis, J. K.; Athersuch, T. J.; Blagrove, M. S.; Herwig, R.; Ebbels, T. M.; Keun, H. C., Consensus-phenotype integration of transcriptomic and metabolomic data implies a role for metabolism in the chemosensitivity of tumour cells. PLoS Comput Biol 2011, 7, (3), e1001113.
26. Pacini, T.; Fu, W.; Gudmundsson, S.; Chiaravalle, A. E.; Brynjolfson, S.; Palsson, B. O.; Astarita, G.; Paglia, G., Multidimensional Analytical Approach Based on UHPLC-UV-Ion Mobility-MS for the Screening of Natural Pigments. Anal Chem 2015.
27. Paglia, G.; Angel, P.; Williams, J. P.; Richardson, K.; Olivos, H. J.; Thompson, J. W.; Menikarachchi, L.; Lai, S.; Walsh, C.; Moseley, A.; Plumb, R. S.; Grant, D. F.; Palsson, B. O.; Langridge, J.; Geromanos, S.; Astarita, G., Ion mobility-derived collision cross section as an additional measure for lipid fingerprinting and identification. Anal Chem 2015, 87, (2), 1137-44.
28. Gonzales, G. B.; Raes, K.; Coelus, S.; Struijs, K.; Smagghe, G.; Van Camp, J., Ultra (high)-pressure liquid chromatography-electrospray ionization-time-of-flight-ion mobility-high definition mass spectrometry for the rapid identification and structural characterization of flavonoid glycosides from cauliflower waste. Journal of Chromatography A 2014, 1323, 39-48.
29. Dong, W.; Wang, P.; Meng, X.; Sun, H.; Zhang, A.; Wang, W.; Dong, H.; Wang, X., Ultra-performance Liquid Chromatography-High-definition Mass Spectrometry Analysis of Constituents in the Root of Radix Stemonae and those Absorbed in Blood after Oral Administration of the Extract of the Crude Drug. Phytochemical Analysis 2012, 23, (6), 657-667.
30. Sun, H.; Ni, B.; Zhang, A.; Wang, M.; Dong, H.; Wang, X., Metabolomics study on Fuzi and its processed products using ultra-performance liquid-chromatography/electrospray-ionization synapt high-definition mass spectrometry coupled with pattern recognition analysis. Analyst 2012, 137, (1), 170-185.
31. Sun, J.; Baker, A.; Chen, P., Profiling the indole alkaloids in yohimbe bark with ultra-performance liquid chromatography coupled with ion mobility quadrupole time-of-flight mass spectrometry. Rapid Communications in Mass Spectrometry 2011, 25, (18), 2591-2602.
32. Stopka, S. A.; Shrestha, B.; Maréchal, É.; Falconet, D.; Vertes, A., Metabolic transformation of microalgae due to light acclimation and genetic modifications followed by laser ablation electrospray ionization mass spectrometry with ion mobility separation. Analyst 2014, 139, (22), 5946-5954.
33. Chory, J.; Chatterjee, M.; Cook, R.; Elich, T.; Fankhauser, C.; Li, J.; Nagpal, P.; Neff, M.; Pepper, A.; Poole, D., From seed germination to flowering, light controls plant development via the pigment phytochrome. Proceedings of the National Academy of Sciences 1996, 93, (22), 12066-12071.
34. Clouse, S. D.; Sasse, J. M., Brassinosteroids: essential regulators of plant growth and development. Annual review of plant biology 1998, 49, (1), 427-451.
35. Phillip, D.; Ruban, A. V.; Horton, P.; Asato, A.; Young, A. J., Quenching of chlorophyll fluorescence in the major light-harvesting complex of photosystem II: a systematic study of the effect of carotenoid structure. Proceedings of the National Academy of Sciences 1996, 93, (4), 1492-1497.
36. Vershinin, A., Biological functions of carotenoids—diversity and evolution. Biofactors 1999, 10, (2), 99-104.
37. Klyachko-Gurvich, G. L.; Tsoglin, L. N.; Doucha, J.; Kopetskii, J.; Semenenko, V. E., Desaturation of fatty acids as an adaptive response to shifts in light intensity 1. Physiologia *Plantarum* 1999, 107, (2), 240-249.
38. Gombos, Z.; Wada, H.; Hideg, E.; Murata, N., The unsaturation of membrane lipids stabilizes photosynthesis against heat stress. Plant Physiology 1994, 104, (2), 563-567.
39. Calder, P. C.; Yaqoob, P., Understanding omega-3 polyunsaturated fatty acids. Postgraduate medicine 2009, 121, (6), 148-157.
40. Simopoulos, A. P., Essential fatty acids in health and chronic disease. The American Journal of Clinical Nutrition 1999, 70, (3), 560s-569s.
41. Sies, H.; Stahl, W., Non-Nutritive Bioactive Food Constituents of Plants: Lycopene, Lutein and Zeaxanthin. International journal for vitamin and nutrition research 2003, 73, (2), 95-100.
42. Stahl, W.; Sies, H., Bioactivity and protective effects of natural carotenoids. Biochimica et Biophysica Acta (BBA)-Molecular Basis of Disease 2005, 1740, (2), 101-107.
43. Jones, P. J.; MacDougall, D. E.; Ntanios, F.; Vanstone, C. A., Dietary phytosterols as cholesterol-lowering agents in humans. Canadian journal of physiology and pharmacology 1997, 75, (3), 217-227.
44. Awad, A. B.; Fink, C. S., Phytosterols as anticancer dietary components: evidence and mechanism of action. The Journal of nutrition 2000, 130, (9), 2127-2130.
45. Glueck, C. J.; Speirs, J.; Tracy, T.; Streicher, P.; Illig, E.; Vandegrift, J., Relationships of serum plant sterols (phytosterols) and cholesterol in 595 hypercholesterolemic subjects, and familial aggregation of phytosterols, cholesterol, and premature coronary heart disease in hyperphytosterolemic probands and their first-degree relatives. Metabolism 1991, 40, (8), 842-848.
46. Hollman, P. C. H.; Katan, M., Dietary flavonoids: intake, health effects and bioavailability. Food and Chemical Toxicology 1999, 37, (9), 937-942.

47. Plumb, G. W.; Price, K. R.; Modes, M. J.; Williamson, G., Antioxidant properties of the major polyphenolic compounds in broccoli. Free Radical Research 1997, 27, (4), 429-435.
48. Gorelik, S.; Lapidot, T.; Shaham, I.; Granit, R.; Ligumsky, M.; Kohen, R.; Kanner, J., Lipid peroxidation and coupled vitamin oxidation in simulated and human gastric fluid inhibited by dietary polyphenols: health implications. Journal of agricultural and food chemistry 2005, 53, (9), 3397-3402.
49. Cartea, M. E.; Francisco, M.; Soengas, P.; Velasco, P., Phenolic compounds in *Brassica* vegetables. Molecules 2011, 16, (1), 251-80.
50. Jahangir, M.; Abdel-Farid, I. B.; Choi, Y. H.; Verpoorte, R., Metal ion-inducing metabolite accumulation in *Brassica rapa*. J Plant Physiol 2008, 165, (14), 1429-37.
51. Podsędek, A., Natural antioxidants and antioxidant capacity of *Brassica* vegetables: A review. LWT-Food Science and Technology 2007, 40, (1), 1-11.
52. Fahey, J. W.; Zhang, Y.; Talalay, P., Broccoli sprouts: an exceptionally rich source of inducers of enzymes that protect against chemical carcinogens. Proceedings of the National Academy of Sciences 1997, 94, (19), 10367-10372.
53. Jahangir, M.; Kim, H. K.; Choi, Y. H.; Verpoorte, R., Health-Affecting Compounds in Brassicaceae. Comprehensive reviews in food science and food safety 2009, 8, (2), 31-43.
54. Zhang, Y., The molecular basis that unifies the metabolism, cellular uptake and chemopreventive activities of dietary isothiocyanates. Carcinogenesis 2012, 33, (1), 2-9.
55. Pérez-Balibrea, S.; Moreno, D. A.; García-Viguera, C., Glucosinolates in broccoli sprouts (*Brassica oleracea* var. *italica*) as conditioned by sulphate supply during germination. Journal of food science 2010, 75, (8), C673-C677.
56. Moreno, D. A.; Carvajal, M.; López-Berenguer, C.; García-Viguera, C., Chemical and biological characterisation of nutraceutical compounds of broccoli. Journal of pharmaceutical and biomedical analysis 2006, 41, (5), 1508-1522.
57. Ciska, E.; Martyniak-Przybyszewska, B.; Kozlowska, H., Content of glucosinolates in cruciferous vegetables grown at the same site for two years under different climatic conditions. Journal of Agricultural and Food Chemistry 2000, 48, (7), 2862-2867.
58. Pérez-Balibrea, S.; Moreno, D. A.; García-Viguera, C., Genotypic effects on the phytochemical quality of seeds and sprouts from commercial broccoli cultivars. Food chemistry 2011, 125, (2), 348-354.
59. Vallejo, F.; Tomás-Barberán, F.; García-Viguera, C., Glucosinolates and vitamin C content in edible parts of broccoli florets after domestic cooking. European food research and technology 2002, 215, (4), 310-316.
60. Goodspeed, D.; Liu, J. D.; Chehab, E. W.; Sheng, Z.; Francisco, M.; Kliebenstein, D. J.; Braam, J., Postharvest circadian entrainment enhances crop pest resistance and phytochemical cycling. Current Biology 2013, 23, (13), 1235-1241.
61. Talalay, P.; Fahey, J. W., Phytochemicals from cruciferous plants protect against cancer by modulating carcinogen metabolism. J Nutr 2001, 131, (11 Suppl), 3027S-33S.
62. McConn, M., The critical requirement for linolenic acid is pollen development, not photosynthesis, in an *Arabidopsis* mutant. The Plant Cell Online 1996, 8, (3), 403-416.
63. Berdyshev, E. V., Mass spectrometry of fatty aldehydes. Biochimica et Biophysica Acta (BBA)-Molecular and Cell Biology of Lipids 2011, 1811, (11), 680-693.
64. Fu, W.; Magnúsdóttir, M.; Brynjólfson, S.; Palsson, B. Ø.; Paglia, G., UPLC-UV-MSE analysis for quantification and identification of major carotenoid and chlorophyll species in algae. Analytical and bioanalytical chemistry 2012, 404, (10), 3145-3154.

What is claimed is:

1. A method of identifying a metabolic pathway containing two or more metabolites, comprising:
   (i) receiving two or more tentative metabolite identification lists, wherein each list comprises potential metabolites having at least substantially the same mass measurement and wherein each list corresponds to a metabolite peak;
   (ii) comparing the two or more tentative metabolite identification lists with two or more known metabolic pathways;
   (iii) identifying at least one metabolic pathway that is statistically more likely to include the two or more metabolites; and
   (iv) analyzing a sample with a mass spectrometry system to generate the at least one metabolic peaks from at least one metabolite to identify at least one of the two or more metabolites, wherein the mass spectrometry system comprises an ion mobility separation.

2. The method of claim 1, further comprising identifying one or more potential metabolites by comparing the mass measurement with metabolite databases.

3. The method of claim 1, wherein the step of identifying at least one metabolic pathway comprises the use of an over-representation analysis tool.

4. A method of identifying a metabolic pathway containing two or more metabolites, comprising:
   (i) receiving a sample containing metabolites;
   (ii) receiving a standard containing metabolites;
   (iii) analyzing the sample with a mass spectrometer system to generate sample metabolite peaks, wherein each sample metabolite peak has a signal intensity, and at least a mass measurement, wherein the mass spectrometry system comprises an ion mobility separation;
   (iv) analyzing the standard with a mass spectrometer system to generate standard metabolite peaks, wherein each standard metabolite peak has a signal intensity and at least a mass measurement, wherein the mass spectrometry system comprises an ion mobility separation;
   (v) comparing the sample metabolite peaks and the standard metabolite peaks to identify one or more altered metabolite peaks having an intensity difference;
   (vi) generating a tentative metabolite identification list for at least two or more of the altered metabolite peaks, wherein each list comprising potential metabolites having at least substantially the same mass measurement;
   (vii) comparing the two or more tentative metabolite identification lists with two or more known metabolic pathways; and
   (viii) identifying at least one metabolic pathway that is statistically more likely to include the two or more metabolites.

5. The method of claim 4 for identifying at least one of the metabolites,
   wherein each list corresponds to a metabolite peak; and analyzing at least one of the metabolic peaks to identify at least one of the metabolite.

6. The method of claim 4, wherein the mass spectrometry system comprises a separation component coupled to quadrupole time-of-flight mass spectrometer.

7. The method of claim 4, wherein the mass spectrometry system further comprises a chromatographic separation coupled to quadrupole time-of-flight mass spectrometer.

8. The method of claim 4, wherein the step of comparing the sample metabolite peaks and the standard metabolite peaks comprises analyzing the sets of peaks using multivariate statistical analyses.

9. The method of claim 8, wherein the multivariate statistical analyses comprise principle component analysis, correlation analysis, partial least squares discriminant analysis (PLA-DA), ANOVA analysis or combinations thereof.

10. The method of claim 4, further comprising identifying one or more potential metabolites by comparing the mass measurement with metabolite databases.

11. The method of claim 4, wherein the step of identifying at least one metabolic pathway comprises the use of an over-representation analysis tool.

* * * * *